(12) United States Patent
Fomenko et al.

(10) Patent No.: US 12,403,221 B2
(45) Date of Patent: Sep. 2, 2025

(54) PREPARATION OF COMPOSITE GELS, POLYMER SCAFFOLDS, AGGREGATES AND FILMS COMPRISING SOLUBLE CROSS-LINKED CHITOSAN AND USES THEREOF

(71) Applicant: NOVOCHIZOL SA, Monthey (CH)

(72) Inventors: Vladislav Fomenko, Novosibirsk (RU); Yuriy Kargapolov, Novosibirsk (RU); Alexey Kharchenko, Novosibirsk (RU); David Sergeevichev, Novosibirsk (RU)

(73) Assignee: NOVOCHIZOL SA, Monthey (CH)

( * ) Notice: Subject to any disclaimer, the term of this patent is extended or adjusted under 35 U.S.C. 154(b) by 0 days.

(21) Appl. No.: 18/681,556

(22) PCT Filed: Aug. 5, 2022

(86) PCT No.: PCT/EP2022/072082
§ 371 (c)(1),
(2) Date: Feb. 6, 2024

(87) PCT Pub. No.: WO2023/012333
PCT Pub. Date: Feb. 9, 2023

(65) Prior Publication Data
US 2024/0277904 A1    Aug. 22, 2024

(30) Foreign Application Priority Data
Aug. 6, 2021 (EP) ..................................... 21190153

(51) Int. Cl.
| | | |
|---|---|---|
| *A61L 27/52* | (2006.01) | |
| *A61L 27/26* | (2006.01) | |
| *A61L 27/48* | (2006.01) | |
| *A61L 27/56* | (2006.01) | |
| *B33Y 70/00* | (2020.01) | |
| *C08J 9/00* | (2006.01) | |
| *C08L 5/08* | (2006.01) | |
| *C12N 5/00* | (2006.01) | |

(52) U.S. Cl.
CPC .............. *A61L 27/52* (2013.01); *A61L 27/26* (2013.01); *A61L 27/48* (2013.01); *A61L 27/56* (2013.01); *B33Y 70/00* (2014.12); *C08J 9/0061* (2013.01); *C08L 5/08* (2013.01); *C12N 5/0062* (2013.01); *C08J 2405/08* (2013.01); *C12N 2533/72* (2013.01); *C12N 2537/10* (2013.01)

(58) Field of Classification Search
CPC .......... A61L 27/52; A61L 27/26; A61L 27/48; A61L 27/56; C08J 9/0061; C08J 2405/08; C08L 5/08; B33Y 70/00; C12N 5/0062; C12N 2533/72; C12N 2537/10
See application file for complete search history.

(56) References Cited

U.S. PATENT DOCUMENTS

2016/0200730 A1    7/2016  He
2018/0000737 A1*   1/2018  Bertonis .............. A61K 9/1652

FOREIGN PATENT DOCUMENTS

| CN | 109 127 690 | 1/2019 | |
|---|---|---|---|
| CN | 110 292 659 | 10/2019 | |
| CN | 112 370 571 | 2/2021 | |
| WO | WO-9312877 A1 * | 7/1993 | .............. B01J 20/24 |
| WO | WO 2019/060740 | 3/2019 | |

OTHER PUBLICATIONS

Written Opinion in International Application No. PCT/EP2022/072082, Feb. 9, 2023, pp. 1-7.
Podorozhko, E.A. et al. "A Study of Cryostructuring of Polymer Systems. 41. Complex and Composite Poly(vinyl alcohol) Cryogels Containing Soluble and Insoluble Forms of Chitosan, Respectively" *Colloid Journal* Jan. 22, 2016, pp. 90-101, vol. 78, No. 1.
Li, Baoqiang et al. "Hyrdrosoluble, UV-crosslinkable and injectable chitosan for patterned cell-laden microgel and rapid transdermal curing hydrogel in vivo" *Acta Biomaterialia*, available online Aug. 25, 2015, pp. 59-69, vol. 22.
Konig, W. et al. "A New Method for Synthesis of Peptides: Activation of the Carboxyl Group with Dicyclohexylcarbodiimide using 1-Hydroxybenzotriazoles as Additives" *Chem. Ber.*, 1970, pp. 1-21, vol. 103.
Losse, V.G. et al. "New Possibilities for Creating the Peptide Bond" *Liebigs Ann. Chem. Bd.*, 1960, pp. 1-12, vol. 636, pp. 1-12.
Anderson, G. W. et al. "N-Hydroxysuccinimide Esters in Peptide Synthesis" 1963, *Ibid*, p. 3039, vol. 85, No. 19.
Arens, J. F. "The chemistry of acetylenic ethers XIII: Acetylenic ethers as reagents for the preparation of amides" *RECUEIL*, 1955, pp. 769-770, vol. 74, Issue 6.
Azzam, D. et al. "Dural Repair in Cranial Surgery Is Associated with Moderate Rates of Complications with Both Autologous and Nonautologous Dural Substitutes" *World Neurosurgery*, May 2018, pp. 1-5, vol. 113.
Bagheri-Khoulenjani, S. et al. "An investigation on the short-term biodegradability of chitosan with various molecular weights and degrees of deacetylation" *Carbohydrate Polymers*, Nov. 17, 2009, pp. 1-4, vol. 78, Issue 4.
Baimenov, A. et al. "A review of cryogels synthesis, characterization and applications on the removal of heavy metals from aqueous solutions" *Advances in Colloid and Interface Science*, 2019, pp. 1-74.
Belleau, B. et al. "A New Convenient Reagent for Peptide Syntheses" *J. Amer. Chem. Soc.*, Mar. 13, 1968, pp. 1651-1652, vol. 6, No. 6.
Bellich, B. et al. "The Good, the Bad and the Ugly" of Chitosans *Marine Drugs*, 2016, pp. 1-31, vol. 14.

(Continued)

*Primary Examiner* — Blessing M Fubara
(74) *Attorney, Agent, or Firm* — SALIWANCHIK, LLOYD & EISENSCHENK

(57) ABSTRACT

The present invention is directed to gels, cryogels and other polymer scaffolds, solid surfaces, aggregates, films and coatings comprising a soluble chemically modified cross-linked chitosan useful for 3D cell and organoid bioprinting and other uses in biology, medicine, bioanalytics and environmental sciences and methods of preparation thereof.

9 Claims, 3 Drawing Sheets

(56) References Cited

OTHER PUBLICATIONS

Bieback, K. et al. "Clinical Protocols for the Isolation and Expansion of Mesenchymal Stromal Cells" *Transfus Med Hemother*, 2008, pp. 286-294, vol. 35.

Bu, H. et al. "Synthesis of a hemoglobin-conjugated triblock copolymer for oxygen carrying and specific recognition of cancer cells" *RSC Adv.*, 2017, pp. 48166-48175, vol. 7.

Cavalcanti, I, D. L. et al. "Pharmaceutical nanotechnology: which products are been designed against COVID-19?" *J Nanopart Res.*, 2020, pp. 1-11, vol. 22.

Çimen, D. et al. "Injectable Cryogels in Biomedicine" *Gels*, 2021, pp. 1-15, vol. 7, No. 38.

Ciuffreda, M. C. et al. "Protocols for in vitro Differentiation of Human Mesenchymal Stem Cells into Osteogenic, Chondrogenic and Adipogenic Lineages" *Methods in Molecular Biology*, 2016, pp. 149-158, vol. 1416.

Dey, M. et al. "3D bioprinting of cells, tissues and organs" *Scientific Reports*, 2020, pp. 1-3, vol. 10, No. 14023.

Diago-Meseguer, J. et al. "A New Reagent for Activating Carboxyl Groups; Preparation and Reactions of N, N-Bis[2-oxo-3-ox-azolidiny/]phosphorodiamidic Chloride" *Synthesis*, Jul. 1980, pp. 547-551 and correction p. 1091.

El-Naggar, M. E. et al. "Hydroxyethyl cellulose/bacterial cellulose cryogel dopped silver@titanium oxide nanoparticles: Antimicrobial activity and controlled release of Tebuconazole fungicide" *International Journal of Biological Macromolecules*, Dec. 15, 2020, pp. 1-5, vol. 165.

Fomenko, V. et al. "Novochizol: a new type of cross-linked chitosan particles for formulation and parsimonious delivery of copper compounds" *Conference, Der Bund Okologische Lebensmittelwirtschaft (BÖLW)*, 2021, pp. 1-20.

Fujino, M. et al. "A New Procedure for the Pentachlorophenylation of N-Protected Amino Acids" *Chem. Pharm. Bull.* 1968, pp. 929-932, vol. 16, No. 5.

Gais, V. H.-J. "4-Dimethylamino-3-butyn-2-one as an Activating Agent for Peptide Synthesis" *Angew. Chem.*, 1978, pp. 1-6, vol. 90, No. 8.

Gorecka, A. et al. "Diethyl Phosphorobromidate—An Effective New Peptide-Forming Agent" *Synthesis*, Jun. 1978, pp. 474-476.

Groll, J. et al. "A definition of bioinks and their distinction from biomaterial inks" *Biofabrication*, Nov. 23, 2018, pp. 1-5, vol. 11.

Gun'ko. V. M. et al. "Cryogels: Morphological, structural and adsorption characterisation" *Advances in Colloid and Interface Science*, 2013, pp. 1-46, vols. 187-188.

Gupta, S. et al. "Evolution of PVA gels prepared without crosslinking agents as a cell adhesive surface" *J Mater Sci: Mater Med*, 2011, pp. 1763-1772, vol. 22.

Gupta, S. et al. "Correction to: Evolution of PVA gels prepared without crosslinking agents as a cell adhesive surface" *J Mater Sci: Mater Med*, 2020, p. 1, vol. 31, No. 63.

Hegarty, A. F. et al. "Peptide Synthesis Using Unprotected Amino Acids and Novel Imidoyl Halide Reagents" *Journal of the American Chemical Society*, Jun. 18, 1980, pp. 4537-4538, vol. 102, No. 13.

Hixon, K. R. et al. "A comprehensive review of cryogels and their roles in tissue engineering applications" *Acta Biomaterialia*, Oct. 15, 2017, pp. 1-6, vol. 62.

Honzl, J. et al. "Amino-acids and peptides. XXXIII. Nitrosyl chloride and butyl nitrite as reagents in peptide synthesis by the azide method; Suppression of amide formation" *Coll. Czech. Chem. Commun.*, 1961, pp. 2333-2344, vol. 26.

Hu, H-B. et al. "Isolation, purification, characterization and anti-oxidant activity of polysaccharides from the stem barks of Acanthopanax leucorrhizus" *Carbohydrate Polymers*, 2018, pp. 359-367, vol. 196.

Jakubke, H-D. et al. "Studies on the Peptide Synthesis of Acylamino Acid Quinolyl-(8)-esters" *A. Chem. Ber.*, 1966, pp. 1-23, vol. 99, No. 8.

Kamat, S. et al. "Nano-engineered tools in the diagnosis, therapeutics, prevention, and mitigation of SARS-CoV-2" *Journal of Controlled Release*, Oct. 2021, pp. 1-57, vol. 338.

Kang, S. et al. "Comparison of pH-sensitive degradability of maleic acid amide derivatives" *Bioorganic & Medicinal Chemistry Letters*, 2014, pp. 2364-2367, vol. 24.

Kharchenko, A. V. et al. "Animals' Brain Electrical Activity Reactions to Various Types of Implants Used to Replace Defects in the Dura Mater" *Polytrauama*, 2022, pp. 1-25, No. 1.

Kharchenko, A. V. et al. "Investigation of the mechanical properties of a composite material of chitosan-vancomycin-nanocellulose nanoparticles of bacterial origin to close dura mater defects" *Free Session, Biomaterial synthesis and characterisation*, WBC2020-3305, 2020, pp. 1-3.

Kinaci, A. et al. "Dural sealants for the management of cerebrospinal fluid leakage after intradural surgery: current status and future perspectives" *Expert Review of Medical Devices*, 2019, pp. 549-553, vol. 16, No. 7.

Kizmazoglu, C. et al. "Comparison of Biomechanical Properties of Dura Mater Substitutes and Cranial Human Dura Mater : An In Vitro Study" *Journal of Korean Neurosurgical Society*, 2019, pp. 1-7, vol. 62, No. 6.

König, W. et al. "A New Method for Synthesis of Peptides: Activation of the Carboxyl Group with Dicyclohexylcarbodiimide using 1-Hydroxybenzotriazoles as Additives" *Chem. Ber.*, 1970, pp. 788-798, vol. 103, abstract only.

Leplawy, M. T. et al. "Peptides-XI: Synthesis of peptides derived from alpha-methylalanine" *Tetrahedron*, 1960, pp. 39-51, vol. 11, Issues 1-2.

Lipovka, A. et al. "The Effect of Adding Modified Chitosan on the Strength Properties of Bacterial Cellulose for Clinical Applications" *Polymers*, 2021, pp. 1-17, vol. 13.

Loroch, Y, "Novochizol™ copper formulations against mildew" *Conference, Der Bund Okologische Lebensmittelwirtschaft (BÖLW)*, 2022, pp. 1-21.

Lozinsky, V. I. et al. "The potential of polymeric cryogels in bioseparation" *Bioseparation*, 2002. pp. 63-188, vol. 10.

Lozinsky, V. I. "Cryogels on the basis of natural and synthetic polymers: preparation, properties and applications" *Russian Chemical Reviews*, 2002, pp. 489-511, vol. 71, No. 6.

Memic, A. et al. "Latest Advances in Cryogel Technology for Biomedical Applications" *Advanced Therapeutics*, 2019, pp. 1-45.

Muduli, S. et al. "Stem cell culture on polyvinyl alcohol hydrogels having different elasticity and immobilized with ECM-derived oligopeptides" *J Polym Eng.*, 2017, pp. 647-660, vol. 37, No. 7.

Nefkens, G. H. L. et al. "A Novel Activated Ester in Peptide Syntheses" *Amer. Chem. Soc.*, Mar. 5, 1961, p. 1263.

Padmaja, P. et al. "Environmental Applications of Chitosan and its Derivatives" *Encyclopedia of Marine Biotechnology*, 2020, pp. 1065-1081.

Paul, R. et al. "N, N'-Carbonyldiimidazole, a New Peptide Forming Reagent" *J. Amer. Chem. Soc.*, Sep. 5, 1960, pp. 4596-4600, vol. 82.

Plieva, F. M. et al. "Cryogel applications in microbiology" *Trends in Microbiology*, 2008, pp. 543-551, vol. 16, No. 11.

Pogorielov, M. et al. "Experimental evaluation of new chitin-chitosan graft for duraplasty" *J Mater Sci: Mater Med.*, 2017, pp. 1-9, vol. 28, No. 34.

Riva, R. et al. "Chitosan and Chitosan Derivatives in Drug Delivery and Tissue Engineering" *Adv Polym Sci.*, 2011, pp. 19-44, vol. 244.

Rosen, C. L. et al. "Results of the Prospective, Randomized, Multicenter Clinical Trial Evaluating a Biosynthesized Cellulose Graft for Repair of Dural Defects" *Neurosurgery*, 2011, pp. 1093-1104, vol. 69.

Saha, A. et al. "Phenolic Ester Mediated Oligopeptide Synthesis Promoted by HOBt" *Protein & Peptide Letters*, 2014, pp. 1-6, Vo. 21.

Sakakibara, S. et al. "The Trifluoroacetate Method of Peptide Synthesis. I. The Synthesis and Use of Trifluoroacetate Reagents" *Bull. Chem. Soc. Jap.*, Nov. 1965, pp. 1979-1984, vol. 38, No. 11.

Sanchez, A. et al. "Esterification of Maleamic Acids without Double Bond Isomerization" *Eur. J. Org. Chem.*, 2010, pp. 2600-2606.

Satchanska, G. et al. "Article; Agriculture and Environmental Biotechnology, Phenol degradation by environmental bacteria entrapped in cryogels" *Biotechnology & Biotechnological Equipment*, 2015, pp. 514-521, vol. 29, No. 3.

(56) References Cited

OTHER PUBLICATIONS

Schmalz, P. et al. "Use of an Absorbable Synthetic Polymer Dural Substitute for Repair of Dural Defects: A Technical Note" *Cureus*, 2018, pp. 1-5, vol. 10, No. 1: e2127.
Shan, L. et al. "Fabrication and use of alginate-based cryogel delivery beads loaded with urea and phosphates as potential carriers for bioremediation" *Ind. Eng. Chem. Res.*, 2016, pp. 1-30.
Shcherban, A.B. "Chitosan and its derivatives as promising plant protection tools" *Journal of Genetics and Breeding*, 2023, pp. 1-12.
Stevens, C. L. et al. "Nitrogen Analogs of Ketenes. V.[1] Formation of the Peptide Bond", *J. Amer. Soc.*, Aug. 5, 1958, pp. 4069-4071, vol. 80.
Vandevord, P. J. et al. "Evaluation of the biocompatibility of a chitosan scaffold in mice" *J Biomed Mater Res.*, 2002, pp. 585-590.
Wieland, T. et al. "A convenient mode of presentation of acylthiophenols and their use in amide and peptide syntheses" *Angew. Chem.*, 1951, pp. 1-11.
Woodward, R. B. et al. "A New Synthesis of Peptides" *J. Amer. Chem. Soc.*, Feb. 20, 1961, pp. 1010-1012, vol. 83.
Zhang, K. et al. ""Bitter-Sweet" Polymeric Micelles Formed by Block Copolymers from Glucosamine and Cholic Acid" *Biomacromolecules*, 2017, pp. 1-25.
Zhao, D. et al. "Biomedical Applications of Chitosan and Its Derivative Nanoparticles" *Polymers*, 2018, pp. 1-17, vol. 10, No. 462.
Zilkha, A. et al. "Preparation of Aspartyl Amides and Peptides via N-Benzyl-DL-aspartic Anhydride Hydrochloride" *Journal of the Chemical Society*, 1957, pp. 4397-4399.

\* cited by examiner

A

B

PREPARATION OF COMPOSITE GELS, POLYMER SCAFFOLDS, AGGREGATES AND FILMS COMPRISING SOLUBLE CROSS-LINKED CHITOSAN AND USES THEREOF

CROSS-REFERENCE TO RELATED APPLICATION

This application is the U.S. national stage application of International Patent Application No. PCT/EP2022/072082, filed Aug. 5, 2022.

FIELD OF THE INVENTION

The invention relates to composite gels and cryogels and other polymer scaffolds, aggregates and films comprising a chemically modified, cross-linked chitosan useful for 3D cell and organoid bioprinting and other uses in biology, medicine, bioanalytics and environmental sciences and methods of preparation thereof.

BACKGROUND OF THE INVENTION

There is an increasing technological interest for advanced materials with improved properties for addressing the needs of emerging applications in life sciences. Recent developments in macroporous materials, cryogels in particular, have demonstrated their very useful applicability as indispensable tools in biomedical research. Cryogels are structured polymeric physical bodies created by cryotropic gelation, a process induced by freezing that generates a solvent-polymer system, in which macromolecules are connected in a three-dimensional network by relatively stable bonds. Cryogels have a macroporous 3D structure with very attractive physical and chemical attributes, such as macroporosity, elasticity, water permeability and ease of chemical modification and have therefore attracted strong research interest in a variety of areas, such as water purification, construction, food technology, catalysis, drug manufacturing, regenerative medicine, biotechnology, bioremediation and biosensors (Memic et al., Advances Therapeutics, 2019, 2, 4, doi.org/10.1002/adtp.201800114; Lozinsky, 2002, Russian Chemical Reviews, 71, 489-511. doi.org/10.1070/rc2002v071n06abeh000720). Cryogels are produced either by branching polymerization or polycondensation of gel precursors, by cross-linking of macromolecular precursors, or physical transformations, such as change in thermodynamic quality of the solvent, partial crystallization or a phase transition of a colloidal sol. Depending on the nature of gel precursors, gelling may occur at different stages of the controlled freeze/thaw cycle, in particular during thawing. Thanks to their sponge-like characteristics, cryogels exhibit high removal efficiency and selectivity for heavy metals, nutrients, and toxic dyes from aqueous solutions but there are challenges when scaling up from lab to commercial scale applications (Baimenov et al., 2020, Advances in Colloid and Interface Science, 276, 102088).

In the biomedical domain, cryogels have been envisioned for the expansion of cell lines, as a vehicle for cell separation, or a tissue engineered scaffold, encouraging regrowth at numerous damaged tissue sites in vivo (Hixon et al., 2017, Acta Biomater, October 15; 62:29-41. doi: 10.1016/j.actbio.2017.08.033.). Cryogels also find applications as bioreactors, as chromatographic matrices, for the separation and capture of viruses and macromolecules, in biosensors, in the construction of organoids and tumoroids, in wound repair and in drug delivery and cell therapies (çimen et al., 2021, Gels, 7, 38. doi.org/10.3390/gels7020038; Memic et al., 2019, supra). Complex microporous poly(vinyl alcohol) (PVA) cryogels have been prepared by cryogenic treatments of PVA-non-cross-linked chitosan hydrochloride solutions (Podorozhko et al., 2016, Colloid Journal, 78 (1), 90-101). However, linear chitosans are likely to negatively impact the physical-chemical characteristics of the formed cryogels because solid material made of chitosan (such as films or threads/tissues) are brittle and poorly extensible, lacking any elasticity.

In agriculture and environmental sciences, cryogels have been proposed for the controlled release of pesticides (El-Naggar et al., 2020, Int J Biol Macromol., 15; 165 (Pt A): 1010-1021. doi: 10.1016/j.ijbiomac.2020.09.226), in soil decontamination (Satchanska et al., 2015, Biotechnology & Biotechnological Equipment, 29:3, 514-52,doi.org/10.1080/13102818.2015.1009167) and in bioremediation (Shan et al., 2016, Industrial & Engineering Chemistry Research, 28, 7655-7660, doi.org/10.1021/acs.iecr.6b01256).

There are however occasional limitations in the use of cryogels as they may exhibit degradability, brittleness, inadequate gel integrity, and rigidity and synthetic polymers may lack bioactivity and bioadhesive properties (Memic et al., 2019 Adv. supra). In such cases, gels, generated by methods other that cryo-gelation may prove beneficial.

Chitosan is a non-toxic, biocompatible, and biodegradable polysaccharide derived from chitin (Bagheri-Khoulenjani et al., 2009, 10.1016/j.carbpol.2009.06.020; VandeVord et al., 2002, 10.1002/jbm.1270). There are numerous confirmed and potential applications of chitosan in a variety of industries and it is actively researched in particular in the biomedical domain (Zhao et al., 2018, Polymers (Basel), 10 (4): 462 doi: 10.3390/polym10040462) and in environmental sciences (Padmaja et al., 2020, Encyclopedia of Marine Biotechnology, doi.org/10.1002/9781119143802.ch42).

As a fully biocompatible polymer, it is an interesting candidate ingredient for composite gels and cryogels. However, chitosan use is limited by its low solubility, both in water at physiological pH and in organic solvents (Riva et al., 2011, doi.org/10.1007/978-3-642-24061-4), its relative physical, chemical and biological instability and heterogeneity (Bellich et al., 2016, Marine drugs, vol. 14, 599, doi: 10.3390/md14050099). Cross-linking techniques have been developed for increasing the solubility and injectability of chitosans but those techniques include UV-induced cross-linking (Li et al., 2015, Acta Biomateriala, 22, 59-69) that generates undesirable radicals that will polymerize and will lead to toxicity concerns.

Therefore, there is an increasing need for the development of macroporous 3D materials which are easy to prepare at a scale-up level from renewable sources for use in a variety of domains.

SUMMARY OF THE INVENTION

The present invention is based on the finding of new uses of a chitosan derivative and methods for its incorporation into materials useful in the biomedical, diagnostic and environmental domains. In particular, the present invention is based on the unexpected finding of a method of preparation of gelling solutions that incorporates a chitosan derivative having advantages of being more biocompatible, bioadhesive, and capable of capture and sustained release of a variety of substances. Those gelling solutions are useful for many applications such as for the preparation of gel systems useful in a number of applications comprising in the field of cell culture, bioprinting, soil enhancing agents and pollutant filtration systems. The methods of the invention allow the incorporation of living cells since those can be performed under very gentle conditions and the solutions used are fully biocompatible. Further applications include surgical material coating which leads to material have long-lasting properties, being fully compatible and which do not create mechanical stress to the neighboring tissues.

An aspect of the invention provides a gelling solution comprising a gel-forming polymer from about 0.3% to about 25% (w/w), a biocompatible acid and a soluble cross-linked chitosan at 0.001% and 20% (w/v) and uses thereof.

An aspect of the invention provides a method for the preparation of a gelling solution and uses thereof, said method comprising the following steps:
  providing a gel-forming polymer in aqueous solution (e.g. from about 0.3% to about 25% (w/w));
  subjecting and maintaining the aqueous solution to a temperature higher than 0° C. but below the boiling temperature (e.g. from about 0° C. to less than 100° C., typically between 80-90° C.);
  adding an acid to the reacting solution under vigorous mixing (e.g. sonication);
  adding a soluble cross-linked chitosan at a concentration from 0.001% to 20% (w/v) to the mixture under vigorous mixing and maintaining the mixing (e.g. sonication) until complete dissolution.

Another aspect of the invention relates to a method for the preparation of a polymeric composite material in the form of a cryogel said method comprising the following steps:
  providing a gelling solution according to the invention at a temperature higher than 0° C. but below the boiling temperature, wherein said gelling solution is amenable to cryo-gelation;
  subjecting the said gelling solution to a gelling-thawing step, wherein the said gelling solution is first frozen (gelling step) and then warmed until thawing, typically at a warming rate not higher than about 1° C. per minute (e.g. 0.03° C. per minute) when the temperature reaches −6° C. and above;
  isolating the obtained macroporous cryogel.

Another aspect of the invention relates to a method for the preparation of a polymeric composite material in the form of a gel said method comprising the following steps:
  providing a gelling solution according to the invention at a temperature higher than 0° C. but below the boiling temperature, wherein said gelling solution is amenable to gelation, other than by cryo-gelation;
  subjecting the said gelling solution to a gelation step other than cryo-gelation;
  isolating the obtained obtaining gel.

Another aspect of the invention relates to a gel or a macroporous cryogel obtainable from a method according to the invention.

Another aspect of the invention relates to a macroporous cryogel material comprising a gel-forming polymer such as polyvinyl alcohol (e.g. from about 0.3% to about 25% (w/w) such as for example from about 0.7% to about 20% (w/w)) and a cross-linked chitosan (e.g. at 0.001% and 20% (w/v.)), said macroporous gel having a three-dimensional structure with interconnected pores of diameter from about 2 to about 50 μm (e.g. typically, the interconnected pores have a diameter comprised between 0.5 and 100 μm) and uses thereof.

Another aspect of the invention relates to a macroporous gel and a gelling solution for use in biology, medicine, bioanalytics, cell and plant cultures and environmental sciences.

Another aspect of the invention relates to a use of a gelling solution or a macroporous gel according to the invention for 3D cell bioprinting.

Another aspect of the invention relates to a method of cell printing including the following steps:
  providing a first volume of a gelling solution according to the invention wherein said first volume of gelling solution is free of cells (cell-free solution) and printing it on a solid surface made of a thermo-conductive material (such as copper, aluminium, silver, stainless steel or any other metal, optionally covered with an inert protective layer) which is cooled to a temperature between −10° C. and −20° C.;
  providing a second volume of a gelling solution according to the invention wherein said second volume of a gelling solution contains a cryoprotectant and cells (cell-containing solution) and printing the mixture on top of the layer of already printed gelling solution;
  repeating sequentially the steps above until the desired number of cell layers has been printed in order to form a multi-layered 3D construct;
  subjecting the multi-layered 3D constructs to a gelling-thawing step.

Another aspect of the invention relates to 3D constructs according to the invention and uses thereof.

Another aspect of the invention relates to a bioink comprising a macroporous gel or a gelling solution according to the invention.

Another aspect of the invention relates to method for printing a three-dimensional structure using a bioink composition according to the invention.

Another aspect of the invention relates to a tissue or organ graft comprising a macroporous polymeric composite material having a three-dimensional structure with interconnected pores of diameter from about 0.5 and 100 μm (e.g. typically interconnected pores have diameter comprised between 2 to about 50 μm), preferably a diameter between 5 and 15 μm), said macroporous polymeric composite material being in the form of a cryogel according to the invention and uses thereof.

Another aspect of the invention relates to a use of a gelling solution, a gel or a macroporous cryogel according to the invention for manufacturing filters, membranes or devices useful for the treatment of biological fluids.

Another aspect of the invention relates to filtering systems such as filters, membranes and/or devices useful for the treatment of biological fluids which comprise a gel or a macroporous cryogel according to the invention.

Another aspect of the invention relates to a cell culture system (e.g. medium or support) comprising a gelling solution, a gel or a macroporous cryogel according to the invention.

Another aspect of the invention relates to a use of a gelling solution, a gel or a macroporous cryogel according to the invention for manufacturing soil enhancement agents.

Another aspect of the invention relates to a soil enhancement agent or material and a method of preparation thereof.

Another aspect of the invention relates to the use of a soluble cross-linked chitosan for the impregnation of materials, in particular cellulose.

Another aspect of the invention relates to the use of a soluble cross-linked chitosan for the preparation of surgical suture threads.

Another aspect of the invention relates a method of preparation of suture threads.

According to another particular aspect, is provided a surgical suture thread comprising a plurality of fibers of a biocompatible polymer, such as bacterial cellulose, collagen, or polyethers or one or more wire of biocompatible metals such as gold, platinum or palladium, those fibers or wires being coated with an aqueous solution comprising a cross-linked chitosan of the invention.

Another aspect of the invention relates to a support material impregnated or coated with a soluble cross-linked chitosan of the invention or with a gelling solution, a gel or a cryogel thereof.

Another aspect of the invention relates to surgical material, in particular surgical material comprising a biocompatible polymer, such as bacterial cellulose, collagen or polyethers or biocompatible metals such as gold, platinum or palladium, wherein said material is coated with an aqueous solution comprising a cross-linked chitosan or a gelling solution, a gel or a cryogel thereof according to the invention.

According to a further aspect, the cross-linked chitosan may be impregnated with a biologically active substance, such as vancomycin, other antibiotics, anti-inflammatory drugs, growth factors or cytokines.

Another aspect of the invention relates to the use of a impregnated bacterial cellulose material according to the invention as a dural substitute.

Another aspect of the invention relates to a dural substitute comprising a bacterial cellulose impregnated with a soluble cross-linked chitosan according to the invention or with a gelling solution, a gel or a cryogel thereof.

Another aspect of the invention relates a use of soluble cross-linked chitosan for the coating of plain or silica-coated magnetic beads.

Another aspect of the invention relates to a plain or silica-coated magnetic bead coated with a soluble cross-linked chitosan according to the invention or with a gelling solution, a gel or a cryogel thereof and uses thereof.

DETAILED DESCRIPTION

Figure 1:
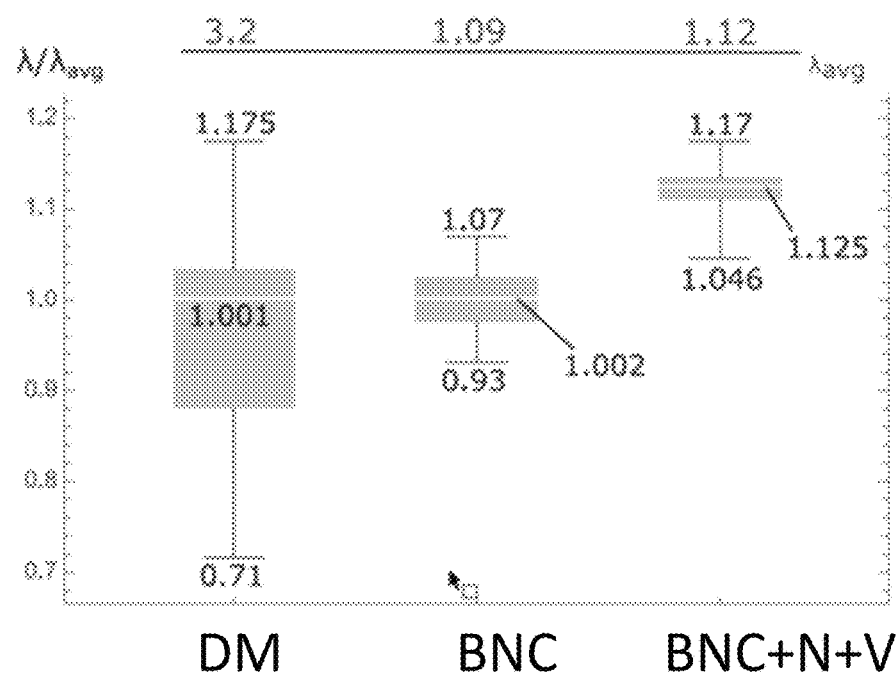
FIG. 1 shows boxplot for values of ultimate strain (A) and stress (B) of human cadaveric dura matter and bacterial cellulose samples, alone or impregnated with cross-linked chitosan and vancomycin as described in Example 5. DM: human cadaveric dura matter, BNC: bacterial cellulose, BNC+N+V: bacterial cellulose impregnated with cross-linked chitosan and vancomycin. The lines (*) and (**) correspond to data of the same value from of DM (Kizmazoglu, et al., 2019, *J. Korean Neurosurg. Soc.*, 62, 635-642. dx.doi.org/10.3340% 2Fjkns.2019.0122) and Tutopatch® material (Parshin, et al., 2020, *In Proceedings of the 11th World Biomaterial Congress*, Online, 11-15).
Figure 1:
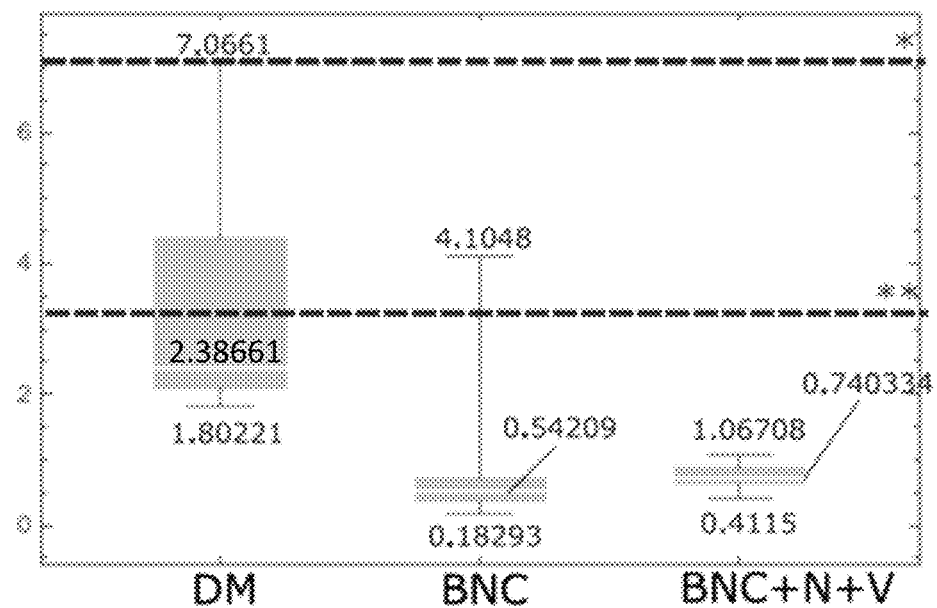

The term "gel system" or "gel" refers to a polymeric physical body comprising an immobilised solvent-polymer system, in which macromolecules are connected in a three-dimensional network by non-fluctuating physical or chemical bonds that are rather stable in time as defined in Lozinsky, 2002, *Russian Chemical Reviews*, 71, 489-511, doi.org/10.1070/rc2002v071n06abeh000720, including in particular polystyrene, polyacrylamide, silicone, agarose, cellulose, starches, gelatin, steroids, nucleic acids, aggrecan/hyaluronic acid.

The expression "biocompatible acid" refers to acids either fully biocompatible such as for example acetic acid, citric acid, propionic acid, caproic acid, aminocaproic acid, succinic acid, glutaric acid, lactic acid, malic acid, tartaric acids, cinnamon acid, and others and partially biocompatible (species-dependent) acids such as for example benzoic acid, sorbic acid, oxalic acid, salicylic acid, acetyl-salicylic, cinnamon acid.

The term "cryogel system" or "cryogel" refers to a gel or a macroporous gel networking developed by the cryogelation of apposite monomers or the polymeric precursors at the subzero temperature such as described in Gun'ko et al., 2013, *Advances in Colloid and Interface Science*, 187-188, 1-46, including: 2-hydroxyethyl methacrylate (2-HOEMA), 2-HOEMA+acrolein, hydroxy- and methoxyoligoglycol methacrylates, oligoethylene glycol monometh-acrylates and dimethacrylates, acryl-amide (AAM) N,N'-methylen-ebis(acrylamide) (MBAAM), AAM+MBAAM+allyl glycidyl ether cryo(silica gel), gelatin+formaldehyde, serum albumin+glutaraldehyde, polystyrene-polybutadiene block copolymer+Pd or Rh salts, collagen+dialdehyde (diepoxide, epichlorohydrin, diisocyanate, etc.), dispersions tanned by heavy metal salts of leather-processing wastes in the presence of cross-linking agents, sodium alginate+calcium gluconate, sodium alginate+calcium salt with a negative temperature factor of solubility, chitosan+beta-tricalcium phosphate, polymeric acids, polymeric bases and polyvinyl alcohol. It also encompasses composite cryogel systems which are cryogels further incorporating another kind of material.

The terms "ink" or "bio-ink" in the context of the present invention refer to a material that is used for 3D printing. In particular, a bioink is the material used to produce engineered (artificial) live tissue using 3D printing technology. This term encompasses the biopolymer gel which acts as a 3D molecular scaffold alone or the biopolymer gel wherein the cells are attached to. Examples of bioinks are presented under Groll et al., 2018, *Biofabrication*, 11 (1), 013001.

The term "soil enhancement agent" refers to an agent that is useful in increasing the soil quality in view of plant culture and growth to resistance to erosion. In particular, this includes agents which reinforce the texture of sols such as silty sands to remedy soil erosion, which enhance soil microflora and water retention properties or assist in bioremediation (e.g. of diesel-contaminated soil by immobilized microorganisms) or favor a faster establishment of plant covers, revegetation with shrub and creeper species.

The term "degree of crosslink" as used herein means the quantity functional groups converted into crosslinking or grafting bonds relative to the total quantity of functional groups initially present on the chitosan, expressed as a percentage.

The term "gel-forming polymer" encompasses a polymer or a mixture of polymers.

The term "amenable to gelation other than cryogellation" refers to a gelling solution that can reach a gel state through a gelling step that is not temperature induced gelling-thawing step, but relies on either chemical cross-linking between the gel constituents resulting in permanent bonds, or physical cross-linking between the gel constituents resulting in temporary bonds induced by changes in pH or temperature, with the exception of gelling-thawing.

The term "amenable to cryogelation" refers to a gelling solution that reaches a gel state after being subjected to at least one cycle of temperature induced gelling-thawing step following the freezing of the liquid present in the solution.

Method of Preparation of a Cryogel According to the Invention and Characterization Thereof According to a particular aspect is provided a process of the preparation of a macroporous composite gel ("composite cryogel") wherein a gel-forming polymer such as polyvinyl alcohol is cryogellified in the presence of a soluble cross-linked chitosan according to the invention.

A chitosan derivative suitable for a method according to the invention is a soluble cross-linked chitosan as described in PCT/EP2021/053204 or any pharmaceutically acceptable salts thereof. In particular, the cross-linked chitosan is obtainable by a method comprising the following steps:
  a) providing a chitosan and leaving the said chitosan to swell in a solvent;
  b) acylating the amino groups of said chitosan with an acrylic compound of Formula (I):

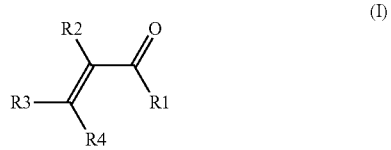

wherein $R_1$ is an a halogen or any other leaving group that upon removal, ensures acylation of an amino group such as 3-hydroxybenzotriazole ester, anhydride (including mixed anhydrides), N-hydroxysuccinimide, pentachlorophenol, 2-nitro-4-sulfophenol esters and other similar leaving groups; $R_2$, $R_3$ and $R_4$ are independently selected from H; optionally substituted alkyl (e.g. $C_1$-$C_6$ alkyl), optionally substituted alkenyl (e.g. $C_2$-$C_6$ alkenyl), optionally substituted alkynyl (e.g. $C_3$-$C_6$ alkynyl), optionally substituted cycloalkyl (e.g. $C_3$-$C_8$-cycloalkyl), optionally substituted cycloalkenyl (e.g. $C_4$-$C_8$ cycloalkenyl), optionally substituted cycloalkynyl (e.g. $C_5$-$C_8$ cycloalkynyl), optionally substituted heterocycloalkyl; optionally substituted aryl (e.g. optionally substituted phenyl), optionally substituted heteroaryl and optionally substituted aryl $C_1$-$C_6$ alkyl, in particular benzyl; wherein the term "substituted refers to groups substituted with from 1 to 5 substituents selected from the group consisting of halogen, —COOR', —NR'R", =O, —OR', —COR', —CONR'R", —SR', —SO$_3$R', —SO$_2$NR'R", —SOR', —SO$_2$R', —NO$_2$, or —CN; or $R_1$ and $R_2$ or $R_1$ and $R_3$, or $R_1$ and $R_4$ together form an optionally substituted 4-24 membered aryl, heteroaryl, cycloalkyl or heterocycloalkyl (e.g. a 6-24 membered aryl, heteroaryl, cycloalkyl or heterocycloalkyl such as an optionally substituted 8-24 membered aryl, heteroaryl, cycloalkyl or heterocycloalkyl);
  c) reacting the acylation product of step b) in the presence of a base (Aza-Michael reaction);
  d) purifying the cross-linked chitosan obtained from step c) (e.g. from salt impurities and/or aprotic solvent).

According to a particular embodiment, the solvent used under step a) and/or b) is a protic solvent (such as alcohols or water).

According to a particular embodiment, the free acrylic acids which are formed if a protic solvent (such as alcohols or water) is used under step a) and/or b) to conduct the process are washed off from the reaction mixture before carrying out step c).

According to another particular embodiment, the solvent is an aprotic solvent, in particular under step a) and/or b) and/or c).

According to a particular embodiment, if an aprotic solvent is used under step c) if no further step f) of subsequent acylation is carried out.

According to a particular embodiment, step a) is conducted at room temperature.

According to a particular embodiment, the R3 or R4 but also R2 groups of the acylated product of step b) will react with the primary amino groups of the glucosamine backbone to form a cross-link between glucosamines. The groups reacting will depend on the specific acrylic compound. For example, for acrylic and methacrylic acids, the groups reacting with the primary amino groups of the glucosamine backbone are groups R3 or R4. However, when R3 and R4 groups are replaced by halogen atoms, then R2 groups will react with the primary amino groups of the glucosamine backbone.

According to a particular aspect, the soluble cross-linked chitosan is fully soluble at pH<5.5 in aqueous solution.

Typically, the soluble cross-linked chitosan has a viscosity that is approximately 3-fold inferior to the original chitosan that was used for its synthesis. The working concentrations, for practical liquid handling reasons, range from 0.01% to 3%.

According to a particular aspect, the soluble cross-linked chitosan has a molecular weight from about 412 Da (2 cross-linked molecules of glucose amine) to about 2 million kDa.

According to a particular aspect, the molecular weight of the soluble cross-linked chitosan is from 2 to about 15 (e.g. about 10) times higher than the molecular weight of the gelling agent.

According to a further particular embodiment, this cross-linking leads to the formation of nanoparticles.

According to a further particular embodiment, the soluble cross-linked chitosan forms a nanosuspension at pH 7.0 or above.

Such a nanosuspension has a lower viscosity than the corresponding solution (at pH<7.0) and can be manipulated as a true solution. In case any precipitate/sediment formation, it can be easily resuspended.

According to particular aspect, the soluble cross-linked chitosan can be obtained by a method schematized under Scheme 1 as follows:

Scheme 1

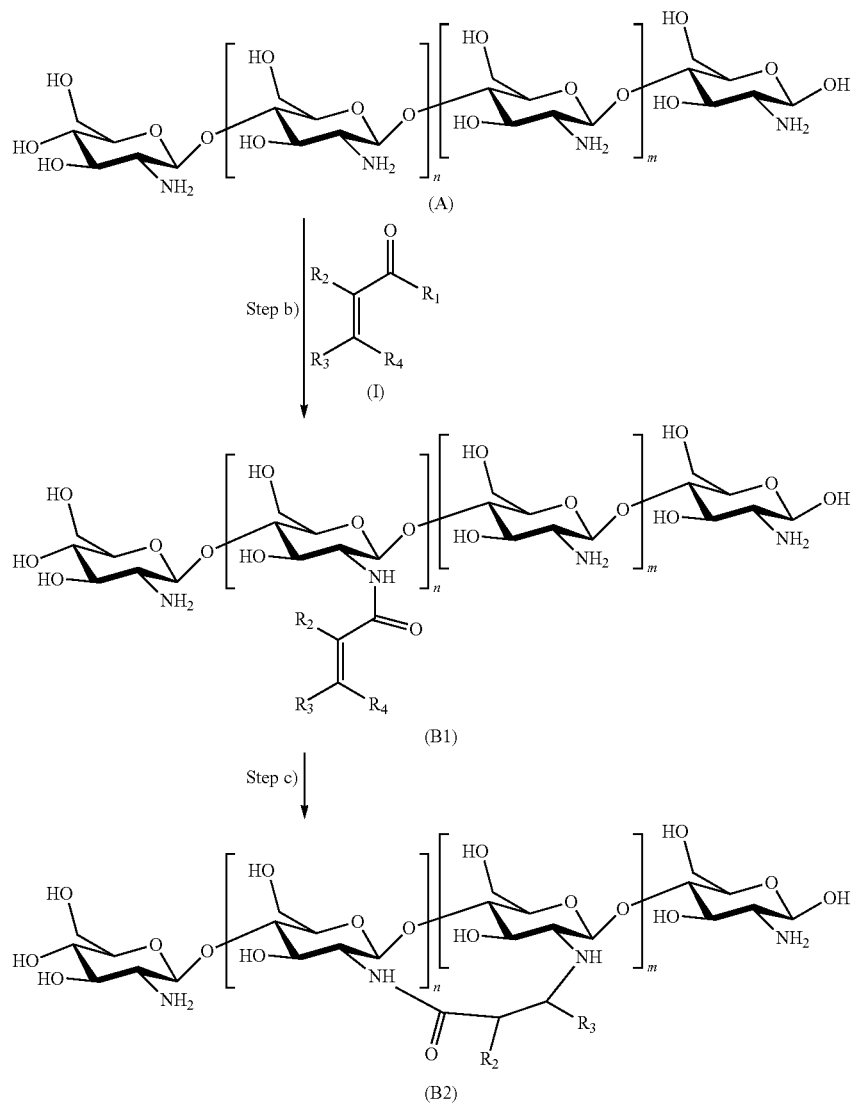

wherein a chitosan (A) wherein m is a integer comprised between 1 and 12'500 and n is a integer comprised between 1 and 12'500, is first provided in a swollen state in an aprotic solvent at room temperature and then the amino groups of said chitosan are acylated with an acrylic compound (I) and the resulting acylation product (B1) is then reacted in presence of a base to lead to a cross-linked chitosan (B2) which can then be isolated by purification to lead to a purified cross-linked chitosan according to the invention.

According to a particular embodiment, the chitosan can be provided in swollen state, even in dissolved state, in a protic solvent but in this case, side reactions of hydrolysis of the acylating agent can occur and this must be taken into account when calculating reaction loads. Additionally, in this case, it will be necessary to wash the acylated chitosan obtained under step b) to remove the hydrolysis products of the acylating agent before the stage of aza-Michael reaction under step c).

According to a particular embodiment, the chitosan is provided in absence of water and the acylating step is carried out in absence of water. The absence of water advantageously leads to higher yields and avoid the formation of side products.

According to a particularly advantageous aspect, the acylation step is conducted in absence of water. In this case, an aprotic solvent can be used as reaction medium or a supercritical fluid. According to a particular embodiment, the aprotic solvent is a polar aprotic solvent such as for example selected from DMF and DMSO. In a particular embodiment, a supercritical fluid can be a supercritical solvent such as carbon dioxide, nitric oxide (I), freons (chloro(bromo)(fluoro)hydrocarbons) which is used to provide the acylating agent to the reaction medium and then acylation reaction carried out after removal of the supercritical solvent from the reaction medium, for example by lowering the pressure below the critical value.

According to a further particularly advantageous aspect, the acylation step is conducted an anhydrous aprotic medium.

According to a particular aspect, a polar aprotic solvent is selected from dimethylformamide (DMF), dimethylacetamide, acetonitrile (MeCN), N-methylpyrrolidone, dimethyl sulfoxide (DMSO) or a mixture thereof.

According to another particular aspect, dichloromethane, dichloroethane, chloroform, and other chloro(fluoro)hydrocarbons can be also used as a polar aprotic solvent, but when conducting the aza-Michael reaction step c), those solvents should be distilled off right before the provision of the base. It is desirable to perform such distillation at temperatures not exceeding 60° C., which is feasible at atmospheric pressure for most of the mentioned solvents. If a high-boiling solvent was used, distillation must be carried out under reduced pressure.

According to another particular aspect, ethers and esters, ketones can also be used as solvents for the reaction steps a) to c) under anhydrous conditions but reactions in such solvents will proceed more slowly. For example, diethyl ether, diisopropyl ether, methyl tert-butyl ether, methyl acetate, ethyl acetate, propyl acetate, butyl acetate, acetone, methyl ethyl ketone and diethyl ketone can be used.

According to a particular aspect, the acylation step b) can be conducted by any method described in the context of acylation of glucosamine with acryloyl chloride (Zhang et al., 2017, *Biomacromolecules*, 1, 3, 778-786; Bu et al., 2017, *Advances*, 7, 76, 48166-48175) or methods described as useful for the acylation of an amino group such as methods using i) a carbodiimide; ii) an azide; iii) mixed anhydrides; iv) an activated ester and v) others methods described below.

Known acylation methods using carbodiimide with the formation of intermediate enol esters can be used under step b) (WO 2019/60740; Hao-Bin et al., 2018, *Carbohydrate Polymers*, 196, 359-367). If N,N'-dicyclohexylcarbodiimide (DCC) can be used as condensing agent, 1-ethyl-(3-(3-dimethylamino) propyl)-carbodiimide hydrochloride and N-cyclohexyl-N'-(2-morpholinoethyl) carbodiimide methyl p-toluenesulfonate (CAS Registry Number: 2491-17-0) would be preferred.

Known acylation methods using azides can be used under step b) (Honzl et al., 1961, *Coll. Czech. Chem. Commun.*, 26, *N*. 9, 2333-2344).

Known acylation methods using mixed anhydrides can be used under step b) (Wieland et al., 1951, *Ann. Chem.*, 572, N3, 190-194; Belleau et al., 1968, *J. Amer. Chem. Soc.*, 90, *N* 6, 1651-1652; Gorecka et al., 1978, *Synthesis, N* 6, 474-476; Diago-Meseguer et al., 1980, *Synthesis, N* 7, 547-551; Leplawy et al., 1960, *Tetrahedron*, 11, *N* 1, 39-51). The use of internal anhydrides is also possible for acylation, for example maleic anhydride (Liwschitz et al. 1957, *Journal of the Chemical Society*, 4399; Kang, et al., 2014, *Bioorganic and Medicinal Chemistry Letters*, 2, 10, 2364-2367; US 2016/200730; Sanchez et al., 2010, *Anna European Journal of Organic Chemistry*, 13, 2600-2606).

Known acylation methods using activated esters through the formation of activated amides can be used under step b) such as a carbonyldiimidazole method (Paul et al., 1960, *J. Amer. Chem. Soc.*, 82, N 17., 4596-4600), a cyanomethyl ester method (Schwyzer et al., 1955, *Helv. Chim. Acta*, 38, *N* 1, 80-83), a thiophenyl ester method (Wieland et al., 1951, supra), a substituted phenyl ester method (Gross et al., 1983, Mayenhofer, editors. Moscow: *Mir., P.* 421), an ester method with heteroaromatic compounds together with carbodiimide method (Jakubke et al., 1966, *A. Chem. Ber.*, 99, *N* 8, 2419-2429; Taschner et al., 1965, *Ann. Chem.*, 690, 177-181), a method of esters with hydroxylamine derivatives together with carbodiimide method (Losse et al., 1964, *Ann. Chem.*, 678, 185-190; Nefkens et al., 1961, *Amer. Chem. Soc.*, 83, N 5, 1263; Anderson et al., 1963, *Ibid*, 85, N 19, 3039; König et al., 1970, *Chem. Ber.*, 103, *N* 3, 788-798), interesterification methods (variant of the ester method) (Sakakibara, 1965, *Bull. Chem. Soc. Jap.*, 38, *N* 1, 1979-1984; Fujino et al., 1968, *Ch. Chem. Pharm. Bull.*, 16, *N* 5, 929-932; Gudkov et al., 1978, 48, 9, 2146; Devadas et al., 1979, *Ind. J. Chem.*, B16, *N* 11, 1026-1027).

Other known acylation methods can be used under step b) such as keteniminie method (Stevens et al., 1958, *J. Amer. Soc.*, 80, *N* 15, 4069-4071); Acetylene derivatives method (Arens, 1955, *Rec. Trav. Chim.*, 74, *N* 6, 759-770; Gais 1978, *Aktivierungsmittel für Peptidsynthesen J. Angew. Chem. Int. Ed*, 90 (8), 625-626 doi.org/10.1002/ange.19780900808); method using derivatives of cyanamide (Losse et al., 1960, *Ann. Chem.*, 636, 144-149); Synthesis using isoxazolium salts (Woodwart et al., 1961, *J. Amer. Chem. Soc.*, 83, *N* 4, 1010-1012); Synthesis using imidoyl halides (Bergmann et al., 1936, *J. Biol. Chem.*, 115, *N* 3, 93-611).

According to a particular embodiment, the acrylic compound of Formula (I) can be an acid, an acid halide, an active ester (e.g. 3-hydroxybenzotriazole ester, N-hydroxysuccinimide, pentachlorophenol, 2-nitro-4-sulfophenol esters and esters having other similar leaving groups), an anhydride or mixtures thereof.

In particular, said soluble cross-linked chitosan is characterized by a mass spectrum pattern comprising a peak with m/z=252.077±0.01 electrospray positive ions.

According to a particular aspect, a soluble cross-linked chitosan suitable according to the invention can be identified be a method comprising the steps of:

providing a chitosan to be characterized in a solvent (e.g. methylene chloride or chloroform);

acylating said chitosan as described herein (e.g. as acetyl chloride or acetic anhydride) under vigorous stirring such as for about 0° C. to about 20° C., such as about 30 minutes;

neutralizing the reaction medium with a base (e.g. diisopropylethylamine as non-nucleophilic base);

evaporating the solvents and washing the obtained neutralized product;

subjecting the product to a reflux acid hydrolysis (e.g. with preferably 28% hydrochloric acid for about 1 to 3 hours, such as about 2 hours);

evaporating the reaction mixture and re-suspending the hydrolysed products in a weak acid such as acetic acid;

determining the presence or absence of a product selected from a product according to Formula (IIIa), or according to Formula (IIIb)

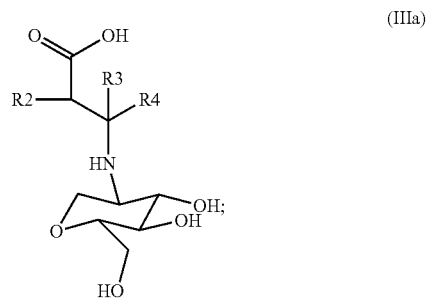

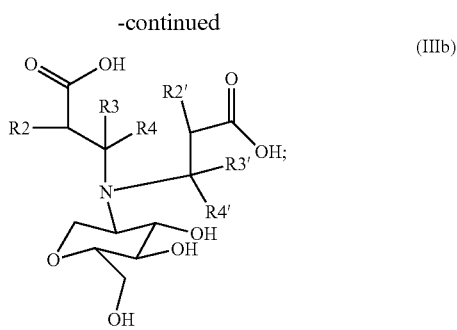

(IIIb)

wherein $R_2$ to $R_4$ are as defined herein, $R_{2'}$ to $R_{4'}$ are as defined respectively as $R_2$ to $R_4$ herein and wherein the presence of a product of Formula (IIIa) and/or (IIIb) is indicative of cross-linked chitosan obtained by a method described above and suitable for formulations according to the invention.

When dissolved, said soluble cross-linked chitosan differs from chitosan in that it generates not a viscous gel, but a low-viscosity suspension compared to linear chitosans. According to a particular aspect, for relatively low concentrations (up to 2% w/v) soluble cross-linked chitosan is 3 times less viscous than chitosan, and up to 10 times less viscous for higher concentrations (above 5% w/v). This property enables rapid diffusion of the soluble cross-linked chitosan particles within the gelling solution.

It is worth noting that the cross-linking for obtaining the soluble cross-linked chitosan according to the invention leads to fundamental structural differences compared to UV crosslinking which leads to double bond polymerization, whereas for obtaining the soluble cross-linked chitosan according to the invention, the double bonds react with the amino groups.

According to a particular embodiment, the soluble cross-linked chitosan, gelling solutions and gels or cryogels thereof enhance the biocompatibility of a material, in particular through coating or impregnation of the material surface.

The said cross-linked chitosan can be used in the form of a dry powder that can be obtained from a method of the invention followed by a freeze-drying step or as an aqueous solution that can be obtained from a method of the invention followed by a dissolution step such as by adding an acidic aqueous solution.

According to a further particular aspect is provided a method for the preparation of polymeric composite material in the form of a macroporous cryogel said method comprising the following steps:

providing a polymer solute in aqueous solution (a gelling solution according to the invention, wherein said gelling solution is amenable to cryogelation) at a temperature higher than 0° C. but below the boiling temperature, said polymer solute solution comprising a gel-forming polymer such as polyvinyl alcohol (e.g. from about 0.7% and to about 20% (w/w)), a biocompatible acid and a soluble cross-linked chitosan at 0.001% and 20% (w/v);

subjecting the said polymer solute solution to a gelling-thawing step, wherein the said polymer solute solution is first frozen (gelling step) and then warmed until thawing at warming rate not higher than about 1° C. per minute (e.g. 0.03° C. per minute) when the temperature reaches −6° C. and above;

isolating the obtained macroporous cryogel.

According to a particular aspect, a macroporous cryogel material according to the invention has a three-dimensional structure with interconnected pores of diameter typically comprised between 0.5 and 100 μm, said macroporous gel material being in the form of a cryogel.

According to a particular aspect, fillers or chemicals (additive) can be admixed to the gelling solution before the gelling step. Depending on the application, the gelling solution may be mixed with any number of substances or materials: chemicals (active ingredients, nutrients, etc.) or fillers: textiles, plant-based materials (cellulose, hemp fibers), other polymers, soil, and, and any other soluble or insoluble material.

According to a further particular embodiment, the additive may be humidified before mixing to facilitate the incorporation of the additive within the gelling solution. Typically, depending on the application and desired hardness, mixtures with a weight ratio (w/w) of 3-10:1 additive: gelling solutions are prepared.

According to another particular aspect, the gelling solution is frozen at a temperature between −196° C.-0° C., such as for example between −10° C. and −20° C.

According to another particular aspect, the frozen gelling solution is warmed up to about 0° C. at warming rate not higher than about 1° C. when the temperature reaches −6° C. and above, e.g. at a rate not higher than about 0.03° C. per minute or not higher than about 0.01° C. per minute. According to a further particular aspect, a waring rate up to about 0° C. at warming rate not higher than about 0.03° C. per minute when the temperature reaches −6° C. allows to obtain a suitable cryogel system. Rates higher than 1° C. per minute lead to a decrease in the cryo-gelation process or even to the absence of cryo-gelation. For concentrations of gelling polymer lower than 5% w/w, the warming rate is not higher than about 0.03° C. when the temperature reaches −6° C.

According to another particular aspect, the frozen gelling solution can be warmed up to about −6° C. at any rate.

According to another particular aspect, a polymer solute aqueous solution (gelling solution) suitable for the invention can be prepared by a method comprising the following steps:

providing a gel-forming polymer in aqueous solution (e.g. from about 0.3% to about 25% (w/w));

subjecting and maintaining the reacting solution to a temperature higher than 0° C. but below the boiling temperature (e.g. from 0° C. to less than 100° C., typically between 80-90° C.);

adding an acid to the reacting solution under vigorous mixing;

adding a soluble cross-linked chitosan at 0.001% and 20% (w/v.) to the mixture vigorous mixing and mixing until complete dissolution.

According to a further particular aspect, a gel-forming polymer is provided in aqueous solution between 2% and 6% (w/w).

According to another further particular aspect, a soluble cross-linked chitosan between 0.25% and 2% (w/v.) is added to the mixture.

Method of Preparation of a Gel According to the Invention and Characterization Thereof According to another aspect, the cryo-gelation, in particular the gelling-thawing step can be replaced by the use of a gelling agent that is not purely physical (temperature change) but would rely on other gelling agents such as photocuring of polymers, radiation curing of polymers, radical curing of polymers, cation curing of polymers, anion curing of polymers, complex formation, complementary interactions, such as the bonding between complementary strands of nucleic acids, standard gelation resulting from changes in temperature or chemical potentials of chemical entities (salts, urea, etc.) such as described in Lozinsky, 2002, supra, thereby leading to an (aqueous) gelling solution which is also useful for the applications described in the current invention.

According to this particular aspect, the gelling solution according to the invention is amenable to gelation other than by cryo-gelation and the gel-forming polymer can be prepared as follows:

- a polyacrylamide, prepared by polymerization of acrylamide at a concentration ranging between 0.05% and 25% (w/v) with bisacrylamide as cross-linking agent at a concentration ranging between 0.01% and 2% (w/v) in water, using two redix initatiors: ammonium persulphate at a typical concentration of 10% (v/v) and tetramethylethylene diamine at a typical concentration of 0.025% (vol/vol); or
- a polystyrene, prepared by copolymerization of styrene and divinyl benzene using azobisisobutyronitrile (2.5 mol %) as an initiator in 4M toluene at 60° C. for about 24 hours; or
- an agarose polymer, prepared by gelling of agarose at a concentration ranging between 0.3% and 4% (w/v) in water by bringing the mixtures to boiling temperature and leaving it to cool below 35° C.; or
- an alginate polymer, prepared by ultraviolet light-activated polymerization of sodium alginate at a typical concentration of 4% (w/v) in the presence of calcium carbonate particles (30 mM) and diphenyliodonium nitrate as a photoacid generator; or
- a DNA polymer, prepared by treating branched DNA fragments with complementary single stranded ends in water at a typical concentration of 5 nmol with T4 DNA ligase (30 Weiss units) at 25° C. over a period of 12 hours; or
- a cellulos-based polymers, prepared by dissolving cellulose in lithium chloride/dimethyl acet-amide, followed by transfer to a non-solvent system, such as azeotropic methanol and isopropanol; or
- a hyaluronic acid hydrogel, prepared by photopolymerization of methacrylated hyaluronic acid and N-vinylpyrrolidone; or
- a polyethylene glycol hydrogel, prepared from polyethylene glycol di-acrylate using V70 as a radical intiator at a temperature of 50° C.

According to this particular embodiment, under the gelation step, the polymers undergo photocuring, radiation curing, radical curing, cation and anion curing, complex formation, complementary interactions, such as the bonding between complementary strands of nucleic acids, or standard gelation resulting from changes in temperature or chemical potentials of chemical entities (salts, urea, etc.).

According to a particular aspect, the soluble cross-linked chitosan allows to prepare cryogels containing high concentrations of gel-forming polymer such as PVA (e.g. up to 25%) and high concentrations of soluble cross-linked chitosan (e.g. up to 20%) which is impossible with linear chitosan.

Gelling Solution According to the Invention

According to a particular aspect, the gel-forming polymer is a polyethylene, in particular polyvinyl alcohol.

According to a particular aspect, the amount of polyvinyl alcohol will determine the softness of the hydrogel. Depending on the applications, polyvinyl alcohol concentrations can be a low as 0.7% and as high as 20%, e.g. typically, final concentration between 5% and 8% (w/w) (for example about 6%) is appropriate for many applications.

According to a particular aspect, the acid can be selected from succinic acid, acetic acid, citric acid or butyric acid, hydrochloric, sulfuric, phoric, oxalic (for some non-cellular applications), acetic, propionic, caprous, succinic, lactic, malic, citric, propane, or butane, or pentane, or hexane-alpha, omega-dicarbonic.

In order to solubilize the cross-linked chitosan, the pH needs to be acid. Once dissolved, the pH can then be changed, thereby leading to a nanosuspension (submicron dispersion of nanosized spheres, stabilized by Brownian motion).

According to a further particular aspect, the acid is succinic acid.

According to a particular aspect, the acid is succinic acid and the gelling solution comprises from about 0.00005% to about 10% succinic acid, for example 0.5% (w/w).

According to a particular embodiment, vigorous mixing comprises sonication (typically 24.5 kHz, 1200 Watt) or by any other means for vigorous active mixing (mixer, pump, adding glass beads).

According to a further particular embodiment, prior to addition to the gelling solution, the cross-linked chitosan may be combined with active ingredients or extracellular factors such as for example by active mixing or sonication, for subsequent sustained release at specific locations from the 3D scaffold, created during the bioprinting process. The technique allows to create spatially defined gradients of any factor, replicating natural processes occurring in organ development. For example, those ingredients can be growth factors, cytokines, chemicals, drugs and extracellular factors include collagen, laminin, elastin and hydrolysates.

According to a particular aspect, sonication is achieved by a sonicator probe immersed in the solution (sonication can be carried out typically at 24.5 kHz, 1200 Watt).

According to a particular aspect, the reacting solution is subjected and maintained to a temperature from about 0° C. to less than 100° C., typically between 80-90° C.) during all the process of the formation of the gelling solution by a hot plate or by sonication.

According to a particular aspect, the amount of succinic acid shall be adjusted to the amount of cross-linked chitosan to be added. Typically, a w/w ratio succinic acid:cross-linked chitosan of 1:2 (w/w) must be reached for dissolution.

According to a particular aspect, the cross-linked chitosan is added slowly to the solution in the form of a powder under vigorous sonication until complete dissolution.

Alternatively, the cross-linked chitosan is added as an aqueous solution that is made by first dissolving an acid in water such as succinic acid (e.g. two-fold amount relative to the cross-linked chitosan), after which the cross-linked chitosan is added slowly to the solution in the form of a powder under vigorous sonication until complete dissolution.

According to a particular aspect, the cross-linked chitosan is added to a final concentration between 0.1% and 20% (w/v), for example 1% (w/v).

According to a further particular aspect, the cross-linked chitosan is added to a final concentration, typically between 0.5% and 2% (w/v), for example 1% (w/v).

Uses of a Cross-Linked Chitosan of the Invention

According to a particular aspect of the invention, a soluble cross-linked chitosan solution, in particular an (aqueous) gelling solution of the invention contains from about 0.001% to about 20% (w/v) soluble cross-linked chitosan, more particularly from about 0.01% to about 20% (w/v), more particularly from about 0.1% to about 20% (w/v), for example from about 0.5% to about 2% (w/v).

According to an independent aspect, the invention further relates to the use of a soluble cross-linked chitosan for the impregnation of various material support.

According to a particular aspect, the material to be impregnated may be a synthetic or a natural polymer, or any composite material that can be covered with liquids. Such materials include polyesters, polypropylene, polyethylene (such as polyvinyl alcohol), polylactide-glycolide, polyamides, polyurethanes, polycarbamates or from cellulose and its derivative, chitosan, chitin, collagen, fibroin (silk), spider silk, casein, lignans, agarose, heparins, pectins, starches, rubber, chaff, any fibreous plant material, slivers, porous metals as such or covered with oxides and other natural and synthetic materials that can act as scaffolds.

According to an independent aspect, the invention further relates to the use of a soluble cross-linked chitosan for the impregnation of a support material selected from cellulose, pure silica or silica coated beads.

When dissolved, the cross-linked chitosan particles are able to efficiently impregnate support materials once applied to said material either directly as a cross-linked chitosan solution or in the form of an (aqueous) gelling solution according to the invention.

According to a particular embodiment, is provided a use of soluble cross-linked chitosan for the coating of plain or silica-coated magnetic beads, useful notably for rapid nucleic acid isolation for example in PCR diagnostics.

According to a further particular embodiment, is provided the use of plain or silica-coated magnetic beads coated with a solution comprising a soluble cross-linked chitosan according to the invention for the capture of nucleic acids (DNA and RNA) present in different samples (DNA and RNA).

In particular, for materials that cannot efficiently accommodate cross-linked chitosan particles, it is possible to use an (aqueous) gelling solution according to the invention to impregnate the material instead of directly a solution of the cross-linked chitosan and subject the impregnated material to a cryogelation step as described herein in order to obtain a composite material.

Uses of a Gelling Solution or a Cryogel According to the Invention

Cryogels have a number of interesting applications in microbiology (Plieva et al., 2008, *Trends in Microbiology*, 16 (11), 543-551, 0966-842X, doi.org/10.1016/j.tim.2008.08.005).

According to a particular aspect, a polymeric composite material in the form of a macroporous cryogel according to the invention can be used as a scaffold for 3D cell bioprinting as described (Dey and Ozbolat, 2020, *Sci Rep* 10, 14023, doi.org/10.1038/s41598-020-70086-y).

According to a particular aspect, is provided a method of manufacturing an ink, in particular a bio-ink for 3D printing comprising a macroporous cryogel according to the invention.

According to a particular aspect is provided a method of 3D printing using a bio-ink according to the invention.

3D cell printing can be carried out in standard bioprinting devices using inks of the following types: pure gelling solutions of the invention, gelling solutions of the invention further containing biologically active substances (growth factors, hormones, developmental factors, extracellular proteins, antibiotics, etc.) and nutrients (e.g. cell growth media, etc.) such as amino acids, sugars, minerals, vitamins, salts, buffers, gelling solutions with cross-linked chitosan impregnated with biologically active substances for achieving a sustained and localized release of those such as growth factors, hormones and cytokines, gelling solutions containing any type of human and non-human mammalian cells (e.g. totipotent stem cells, natural and induced pluripotent stem cells, progenitor cells, differentiated cells, transformed, neoplastic and immortalized cells, etc.), gelling solutions containing any type of microorganism (e.g. eubacteria, archae, protists, fungi, algae), gelling solutions containing modified cells (e.g. spheroplasts or protoplasts), organelles (e.g. mitochondria or chloroplasts) or viruses. Different inks containing different cell types and different substances as described above may be used to bioprint organoids of great complexity with a high precision.

According to a particular aspect, is provided a method of cell printing including the following steps:
    providing a first volume of an (aqueous) gelling solution according to the invention wherein said first volume of gelling solution is free of cells (cell-free solution) and printing it on a solid surface made of a thermo-conductive material (such as copper, aluminium, or silver) which is cooled to a temperature between −10° C. and −20° C.;
    providing a second volume of an (aqueous) solution according to the invention wherein said second volume of a gelling solution contains a cryoprotectant and cells (cell containing solution) and printing the mixture on top of the printed layer of the pure gelling solution;
    repeating sequentially the steps above until the desired number of cell layers have been printed in order to form a multi-layered 3D construct;
    subjecting the multi-layered 3D constructs to a gelling-thawing step.

The two steps above are repeated until the desired number of cell layers (with any number of desired additives) have been printed in order to form a multi-layered 3D scaffold. Typically, from about 10 to about 100 cell-containing layers could be applied for tumoroids and it can be thousands for organoids or tens of thousands for organ printing. The formed scaffold is then warmed up to 0° C. or above. Warming up to −6° C. may be fast, but subsequent warming (above −6° C.) must be very slow, preferably at a rate of below 0.01° C. per minute to form a 3D gel. After gelling, an aggregate of cells is formed and the scaffold is washed to remove any harmful substances that may be present (radical initiators, acids, bases, excipients, etc.) and transferred to culture medium to sustain growth and metabolism. The formed aggregates can then be used for tissue engineering, disease modelling, making organoid, tumoroid.

According to a particular aspect, the printing of the gelling solution can be carried out as charged or neutral microdrops or aerosols, under a temperature between 10° C. and −20° C.

According to a particular embodiment, a polymeric composite material in the form of a macroporous cryogel according to the invention can be used for the preparation of a variety of 3D constructs that imitate specific organs or living structures, with the ultimate objective of organ printing such as described in Zhang et al., 2021, *Materials & Design*, 199, 109398, doi.org/10.1016/j.matdes.2020.109398. For instance, film templates comprising a macroporous gel according to the invention formed by lithographic or other known methods may be used to direct printing of vasculature, nerve bundles and ultimately vascularized tissue.

According to a further particular embodiment, 3D constructs which can be prepared according to a method of the invention include organoids (useful in research in developmental biology and regenerative medicine, toxicology and other basic research and applied domains), tumoroids (useful in research in oncology) and engineered tissues and grafts (e.g. as artificial, living cartilage or to cover implants when more solid matrices are required such as in artificial bone tissue).

According to a particular aspect, the 3D pattern/scaffolds produced according to the invention can be usefully used in regenerative medicine.

According to a particular aspect, the 3D printed cryogel can be advantageously used in mammalian cell culture for the manufacturing of biologicals (such as biopharmaceuticals) as an anchoring support for cells allowing those to survive and carry out an active metabolism.

According to another particular aspect, a cell-containing gelling solution according to the invention further comprising a cryoprotectant can be formulated as microparticles. For example, the cell-containing gelling solution can be passed through a cell sorter where every cell-counting droplet is deposited on a frozen surface and thawed like in bioprinting, thereby forming microparticles of cryogel. Cryogel microparticles up to 500 µm in size, preferably up to 150 µm, will be used as a carrier for the growth of adhesive cells. The cells will adhere by their own attachment mechanisms to the cross-linked chitosan present in the cryogel. The porosity will provide an increase in the area of each particle and an increase in the number of cells located on each microparticle. The use of a bioreactor (e.g. 1 liter or more) allows the rapid production of a large number of cells for subsequent use (auto-, allo- or xenogeneic transplantation, creation of implants for human and animal treatment, creation of organoids from healthy and/or tumor cells for pharmaceuticals and then used for cell culture in liquid medium at a high density in a bioreactor. This approach allows achieving improved cell viability and higher rates of gene expression, protein production, cell differentiation.

According to another particular aspect, a cell-seeded cryogel according to the invention can be used for the immobilization of microorganisms (bacteria, yeast, etc.) in fermentation procedures, to improve viability, metabolism, and yields of the product being biomanufactured.

According to another aspect, is provided a use of the polymeric composite materials in the form of a macroporous cryogel according to the invention for manufacturing filters, membranes or devices for the treatment of biological fluids. In particular, the macroporous cryogel according to the invention has the capacity to absorb a variety of potentially harmful molecules (heavy metals and other xenobiotics) that may negatively impact cell viability and proliferation.

According to a particular embodiment, is provided a use of a macroporous cryogel according to the invention as a soil enhancement agent.

According to a particular embodiment, is provided a method of preparation of a soil enhancement agent comprising the following steps:
  providing a polymer solute aqueous solution (gelling solution) at a temperature higher than 0° C. but below the boiling temperature, said polymer solute solution comprising comprising a gel-forming polymer such as a polyvinyl alcohol (e.g. 0.7% and as high as 20% (w/w)), a biocompatible acid and a soluble cross-linked chitosan at 0.001% and 20% (w/v), wherein said gelling solution optionally further comprises seeds;
  mixing the gelling solution with soil to obtain a soil enhancement agent.

According to a particular embodiment, the gelling solution is mixed with soil at a ratio of about typically 3:1 (w/w) soil: gelling solution.

The soil enhancement agent can then be strewn over a soil surface and mixed to the soil.

In temperate climate regions, the soil enhancement agent can be mixed to the soil during the warm season and the gelation of the gelling solution will occur on itself on site during the cold season.

Alternatively, the mixture of the gelling solution and soil is subjected to a gelling-thawing step, wherein the mixture is first frozen (gelling step) and then warmed until thawing at warming rate not higher than about 0.1° C. per minute, in particular not higher than 0.03° C. per minute when the temperature reaches −6° C. and above. The obtained cryogel is useful for use in soil treatment.

According to a particular aspect, the mixture of the gelling solution containing seeds/tubercules/seedlings and soil can be used subjected to a gelling-thawing step, wherein the mixture is first frozen (gelling step) and then warmed until thawing at warming rate not higher than about 0.03° C. per minute when the temperature reaches −6° C. and above to obtain cryogel supported seed material for later use in agriculture. In the so-obtained material, the seeds, tubercules or seedlings are individually embedded in cryogel compartments and can be used for culture treatment such as stratification, pre-germination or as a protection (for example in mechanical sowing).

According to a particular aspect, a soil enhancer according to the invention can be used to elicit plant immune defenses and promote resistance to plant pathogens.

According to a particular aspect, a soil enhancer according to the invention can be used to capture and retain soil pollutants (such as heavy metals).

According to a particular aspect, boronic acid may be added to the gelling solution. In that case, a water impermeable complex is immediately formed at the surface of contact, in the absence of freezing. This impermeable complex can be sued for the purposes of trapping cells (in biomedical application) or create surfaces that resist water erosion (in soil remediation applications).

According to a further particular embodiment, a gelling solution according to the invention may be treated with boric acid or borate salts in the form of a solution (spray) or powder in order to render it impermeable and stabilize the gel in situ in case of heavy rains or run-off.

According to a further particular embodiment, a gelling solution or a cryogel according to the invention can be used for the impregnation or coating of various materials, in particular cellulose fibers, in particular bacterial cellulose.

According to a further particular aspect, the invention further relates to the use of a soluble cross-linked chitosan for the preparation of surgical suture threads.

The impregnation of fibers can be carried out by standard methods such as electrospinning.

According to a particular aspect, a cross-linked chitosan solution is applied to said material in liquid form or as an aerosol.

According to another particular aspect, is provided a method of preparation of suture threads, said method comprising the steps of:
  providing a plurality of fibers of a biocompatible polymer, such as bacterial cellulose, collagen, or polyethers or one or more wire of biocompatible metals such as gold, platinum or palladium, those fibers or wires;
  coating said fibers or wire with an aqueous solution comprising a cross-linked chitosan of the invention.

According to another particular aspect, is provided a surgical suture thread comprising a plurality of fibers of a biocompatible polymer, such as bacterial cellulose, collagen, or polyethers or one or more wire of biocompatible metals such as gold, platinum or palladium, those fibers or wires being coated with an aqueous solution comprising a cross-linked chitosan of the invention.

According to a further particular aspect, surgical suture threads of the invention present the advantages of having a long lifetime in tissues (e.g. about 18 months), being fully biocompatible and surface properties avoiding mechanical stress to the tissues surrounding the suture.

Another aspect of the invention relates to a support material impregnated or coated with a soluble cross-linked chitosan of the invention or with a gelling solution, a gel or a cryogel thereof.

Another aspect of the invention relates to surgical material, in particular surgical material comprising a biocompatible polymer, such as bacterial cellulose, collagen or polyethers or biocompatible metals such as gold, platinum or palladium, wherein said material is coated with an aqueous solution comprising a cross-linked chitosan or a gelling solution, a gel or a cryogel thereof according to the invention.

According to a further aspect, the cross-linked chitosan may be impregnated with a biologically active substance, such as vancomycin, other antibiotics, anti-inflammatory drugs, growth factors or cytokines.

According to another particular aspect, is provided a method of coating a material, said method comprising a step of immersing the material (wetting) in a solution comprising a cross-linked chitosan of the invention, optionally while mechanical mixing or sonication, or a step of spraying (e.g. electrospraying) a solution comprising a cross-linked chitosan of the invention on the surface of the material.

According to a further aspect of the invention, impregnation or coating of the material is achieved with a solution comprising a soluble cross-linked chitosan of the invention containing at least 0.001% w/W of soluble cross-linked chitosan (e.g. from about 0.001% and 20% (w/v)). However, it is possible to repeat impregnation or coating steps several times and each time the material is enriched until saturation state which depends on the nature of the material.

According to another particular aspect, the material or support (e.g. bead) may be pre-treated, prior to applying the soluble cross-linked chitosan by covalently linking it to compounds that contain terminal groups, such as epoxy, aldehyde, alkyl halogen, isocyanate, and other analogous groups that react with amino groups (or hydroxygroups). Such pre-treatment leads to covalent links with the soluble cross-linked chitosan. Similarly, the soluble cross-linked chitosan, once absorbed by the material or support (e.g. bead) may be further cross-linked by the addition of alpha-omega halogen alkyls, such as diglycidyl alkyls, in particular ethylene glycol diglycidyl ether, 1,2-dibromoethane, 1-3-dibromopropane, alpha-omega diglycidil, glutaraldehyde and other dialdehydes, di-isocyanate compounds, and di-iso-thiocyanate compounds. If additional cross-lining creates tertiary amino groups, they can be quaternized by alkyl iodides.

According to another particular aspect, the material is added to a gelling solution and the mixture is subjected to cryogelation according to the invention, resulting in multi-component cryogels. In all cases, the cross-linked chitosan may first be impregnated with biologically active ingredients for their sustained release in the final product.

According to a particular aspect, the impregnation enhances the impregnated material's biocompatibility and confers additional properties. Of particular interest are materials that contain pores or conduits that can accommodate particles of the size of cross-linked chitosan (approx. 20 nm in diameter). As an example, the impregnation of bacterial nanocellulose is extremely uniform to a depth of at least 1 mm. Such an impregnation makes it possible to preserve or enhance the original characteristics of the material (such as its mechanical properties or capillarity) and add new, cross-linked chitosan-specific properties, such as biocompatibility and sustained release of biologically active ingredients.

Materials that contain pore sizes that can accommodate cross-linked chitosan particles include both polymers (such as cellulose, chitin, polyamide fibers, polyethylene, polyethers) and inorganic or composite materials (metals used in implants, ceramics, Metal-organic frameworks (MOFs), metals with oxide or nitrite plating). The rapid rate of diffusion of cross-linked chitosan particles, their temperature resistance, and strong adherence allow impregnation of various material over short periods of time, sterilization by autoclaving, and uniform and robust coating of the surfaces that are impregnated.

Coated materials and supports according to the invention may be used in the following biomedical applications:

1. In traumatology: coating of osteosynthesis systems for fractures at all locations, intraosseous osteosynthesis systems for hips, ships, shoulders, external fixation systems, hip and knee prostheses, gamma nails, cages for ventral spondylodesis).
2. In neurosurgery: coating of cranioplasty plates made of various metals, including plates made by sintering on a 3D printer, spine transpedicular fixation systems, cages for intervertebral disc replacement, cross-linked chitosan ceramic catheterization for interbody fusion, duraplasty using cross-linked chitosan-impregnated bacterial cellulose alone or with added antibiotics (in case of infection).
3. In dentistry: coating of dental implant pins.
4. In maxillofacial and thoracic surgery: coating of implants for the fixation of facial skeletal fractures and deformities, alveolar, transbuccal and biodegradable resorbable plates. Patient-customized implants, sternal fixation implants, systems for rib fracture stabilization/correction of thoracic deformities.
5. In general surgery: cross-linked chitosan-containing hemostatic materials, composite materials: cross-linked chitosan-bacterial cellulose, wound dressings that promote better healing and the prevention of scar complications (in non-infected wounds).
6. In plastic surgery: cross-linked chitosan-bacterial cellulose coating of silicone gel breast implants.
7. In cosmetology: cosmetic masks of different compositions (hyaluronic acid, other acids, amino acids, lactic acid, etc.).
8. In purulent surgery and cambustiology-cross-linked chitosan-bacterial cellulose impregnated with antibiotics for treatment of purulent and infected wounds and infected burns.
9. In endovasal and cardiovascular surgery: coating of endovascular microcoils and intracranial stents for treatment of cerebral aneurysms; stent-retrievers for thrombus removal in ischemic strokes.
10. In vascular surgery: coating of artificial vessels with cross-linked chitosan-bacterial cellulose.

Examples illustrating the invention will be described hereinafter in a more detailed manner and by reference to the embodiments represented in the Figures.

EXAMPLES

The following abbreviations refer respectively to the definitions below:
DMEM (Dulbecco's Modified Eagle Medium).

Example 1: Preparation of Cryogels According to the Invention

A cryogel according to the invention was prepared as follows.
a) Providing a Polymer Solute Aqueous Solution (Gelling Solution) According to the Invention
A gelling solution was prepared by:
1. providing a polyvinyl alcohol aqueous solution (6% (w/v)), subjecting and maintaining the reacting solution at 120° C. for 30 minutes;
2. adding succinic acid at 0.5% w/w to the reacting solution under sonication (24.5 kHz, 1200 Watt);
3. adding a cross-linked chitosan 1% (w/v) prepared as described in PCT/EP2021/053204 (Novochizol™) to the mixture under sonication (typically 24.5 kHz, 1200 Watt) and maintaining the sonication until complete dissolution.

b) Subjecting the Said Polymer Solute Solution to a Gelling-Thawing Step

The obtained gelling solution was poured into a 25×80 mm Teflon dish and a 50 µm film at the bottom of the dish was molded by introducing a specially designed Teflon bloc into the dish that exerts a pressure on the gelling solution to form a film.

The mold with the plunger still in place was the frozen at −20° C. and subsequently warmed in two stages: rapid warming to −6° C., followed by slow warming (0.01° C. per minute) to +4° C. The mold was then dissembled and the obtained cryogel film used to seed cells as described below.

Example 2: Use of Cryogels According to the Invention for Cell Culture

Polyvinyl alcohol gels in themselves can be used as a matrix for cell adherent cultures, but bioadherence is suboptimal (Muduli et al., 2017, *Journal of Polymer Engineering*, 37 (7), pp. 647-660. doi.org/10.1515/polyeng-2016-0193). Advantages of cryogels according to the invention, notably in their capacity to support mammalian cell culture due to strong bioadherent properties have been assayed as follows. Those bioadherent properties ensure cell anchoring, a necessary condition for the culturing of many mammalian cell lines (adherent cell cultures).

Cell Preparation

Human bone marrow mesenchymal stem cells (MSCs) were collected from healthy donors through bone marrow aspiration and isolated as described (Bieback et al., 2008, *Transfus Med Hemother.*, 35 (4): 286-294, doi: 10.1159/000141567) through 1,077 g/ml density gradient centrifugation, followed by 2 washes and grown in DMEM growth medium containing 10% MesenCult™ fetal serum, l-glutamine and antibiotics. The purity of the culture was verified using flow cytometry. The cultured MSCs displayed the following phenotype: CD44+/CD73+/CD90+/CD105+/CD34−/HLA−DR− with a demonstrated capacity for chondrogenic, osteogenic and adipogenic differentiation upon addition of specific media as described (Ciuffreda et al., 2016, *Methods Mol Biol.*, 1416:149-58. doi: 10.1007/978-1-4939-3584-0_8). The study employed cells at 4 passages.

Cell Culture

The walls of 25 cm$^2$ culture dishes were covered with the cryogel of the invention obtained as described in Example 1, the dishes were washed twice with cell growth medium and seeded with the MSCs prepared as described above. Untreated culture dishes of the same size were similarly seeded for comparison. The presence of the cryogel of the invention on the plastic walls of culture dishes did not interfere with cell attachment and cell growth. Within 3-4 hours after inoculation, the cells spread and adopted their characteristic spindle-like shape. It was observed that the cryogel of the invention ensures the adherence and sustain the growth and proliferation of human bone marrow mesenchymal stem cells, under conditions where standards PVA cryogels are problematic (Gupta et al., 2011, *J Mater Sci Mater Med.*, 22 (7): 1763-72. doi: 10.1007/s10856-011-4343-2. Epub 2011 Jun. 4. Erratum in: *J Mater Sci Mater Med.* 2020 Jul. 21; 31 (8): 63. PMID: 21643819).

Those data support that a cryogel according to the invention can be advantageously used for cell culture since an increased viability is observed.

Example 3: Use of a Gelling Solution According to the Invention in Soil Restoration A soil enhancement agent according to the invention was prepared as follows:
a) Providing a Polymer Solute Aqueous Solution (Gelling Solution) According to the Invention
A gelling solution comprising a polyvinyl alcohol aqueous solution (6% (w/v)) succinic acid at 0.5% w/w and a soluble a cross-linked chitosan 1% (w/v) was prepared as described under Example 1 a).
b) Mixing the Gelling Solution with Soil The gelling solution was mixed with sand in a 3:1 (w/v) ratio to obtain a soil enhancement mixture according to the invention. The mixture was then transferred to wooden crates, creating a layer of an approximate thickness of 1 cm. The mixture was seeded with Bluegrass seeds (*Poa pratensis*, Balin variety), at a depth of 1-2 mm with 1 cm spacing. A control crate, containing only sand was also equally seeded.

The crates were placed in a freezer room at a temperature of −20° C. for a period of 10 allowed to warm slowly in a cold room to a temperature of +6° C. The rate at which temperature increased was kept under 0.01° C. per minute. The contents of the crates were then placed in soil during the month of July in the region of Novosibirsk, Russia and left to germinate under natural conditions, with regular watering to keep all soil equally moist.

Seeds in the soil enhancement mixture according to the invention germinated after 7 days, while those in the control after 12 days. One month after the beginning of the experiment, germination rates reached nearly 100% in the soil enhancement mixture (versus 92% in the control). A two-week lag in plant growth in the control remained throughout the growing season, lasting till October.

Those data support that a cryogel/gelling solution according to the invention can be advantageously used as a soil enhancement mixture. In particular, a cryogel/gelling solution according to the invention promotes a faster germination which advantageously reduces loss in the field caused by birds feeding on the freshly sown seeds and act as a plant growth elicitor and consolidates soil to prevent erosion.

Example 4: Cross-Linked Chitosan Impregnation of Bacterial Cellulose for Dural Repair and Other Clinical Applications Dura mater, the connective tissue membrane that surrounds the brain and the spinal cord, must be meticulously closed after craniotomy procedures or in case of injury or some brain tumors. Such closure must prevent any leakage of the cerebrospinal fluid. Current methods remain unsatisfactory in that respect (Kinaci and Van Doormaal, 2019. *Expert Rev Med Devices* 16, 7, 549-553. doi.org/10.1080/17434440.2019.1626232).

Duraplasty is a common procedure that consists in applying a dural patch or dural substitute. The rationale is to provide a watertight scaffold for endogenous dural repair to proceed flawlessly (neodura formation). Current dural substitutes comprise biological grafts, which are difficult to obtain and may expose patients to viral infections or prion diseases, synthetic polymers (Azzam et al., 2018, *World Neurosurg.*, 113, 244-248, doi.org/10.1016/j.wneu.2018.01.115; Schmalz et al., 2018, *Cureus*, 10 (1), e2127, dx.doi.org/10.7759% 2Fcureus.2127) and biopolymers (Pogorielov et al., 2017, *J. Mater. Sci. Mater. Med.*, 28, 34. doi.org/10.1007/s10856-017-5845-3; Rosen et al., 2011, *Neurosurgery*, 69, 1093-1104, doi.org/10.1227/neu.0b013e3182284aca. Liquorrhea (leakage of cerebrospinal fluid), a common complication after craniotomy, leads to communication of the cranial cavity with the external environment. It often leads to the development of severe purulent complications from the central nervous system, requiring antibiotherapy and repeated surgical interventions aimed at sealing the cranial cavity and spinal canal with the additional imposition of repeated sealed sutures on the dura mater. There is an unmet need for an effective, standardized dural substitute (Lipovka et al., 2021, Polymers, 13, 1995, doi.org/10.3390/polym13121995).

Cross-linked chitosan according to the invention was used to prepare an antibiotic-laden bacterial-cellulose dural substitute as follows:

1. Cross-linked chitosan aqueous solutions were obtained by dissolving succinic acid in water (500 mg per 100 ml sterile water), gradually adding cross-linked chitosan (1'000 mg of Novochizol™ per 100 ml succinic acid solution) to the acidic solution under sonication, and sonicating the mixture for one hour, using model UZTA-0.4/22-OM sonicator (U-sonic, Biysk, Russia) at maximum power. Sterile water was added to compensate for evaporation caused by the prolonged sonication.
2. The solution was filter-sterilized using 0.45 μm apyrogenic acetate cellulose filters (Minisart®, Sartorius Stedim Biotech Göttingen, Germany). Thereafter, 1'000 mg of vancomycin hydrochloride was added to the resulting solution, and the solution was subjected to the same ultrasonic treatment for 5 min. The solution was filter-sterilized again using 0.45 μm apyrogenic acetate cellulose filters (Minisart®, Sartorius Stedim Biotech Göttingen, Germany), then stored as a 1% stock at +4° C. and used within one week.
3. Samples of bacterial cellulose obtained by standard cultivation in the medium of the bacterial strain *Komagataeibacter Xylinus* JCM 7644 were individually immersed in the cross-linked chitosan solution above in a plastic tube (50 mL) at a ratio of sample volume to solution of 1:10. The samples impregnated with cross-linked chitosan with were then treated with an ultrasonic bath at +37° C. for 10 min., neutralized with 1M aqueous ammonia to pH7, washed with sterile water and stored at +4° C.

Figure 2:
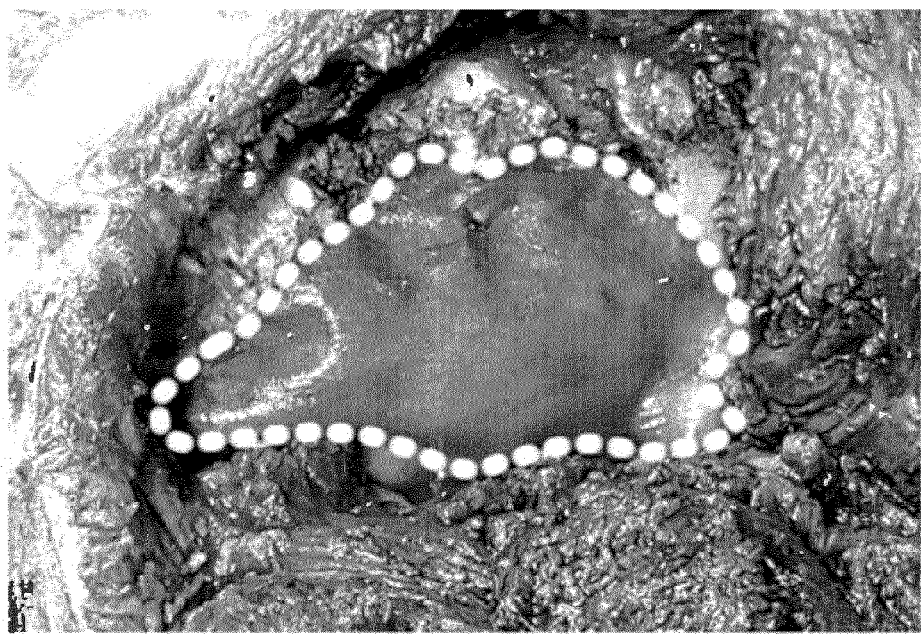
FIG. 2 shows the post-surgery appearance of duraplasty conducted in a dog model using commercial opaque Lyoplant™ dural substitute (A) and transparent bacterial cellulose impregnated with cross-linked chitosan and vancomycin (B) according to the invention as described in Example 5. The white, dotted line indicates the area where duraplasty was carried out.
Figure 2:
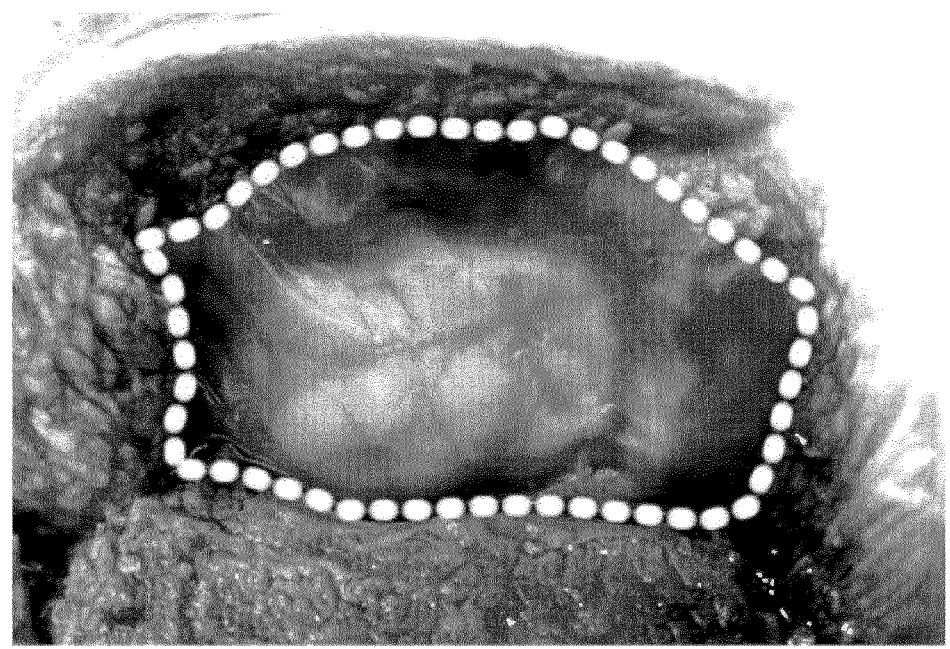

The strength of the obtained impregnated bacterial cellulose (BNC) samples was compared to those of human cadaveric dura matter tissues (DM) (Lipovka et al., 2021, Polymers, 13, 1995. doi.org/10.3390/polym13121995). Impregnation with cross-linked chitosan provided a statistically significant impact on the strength properties (FIG. 1) and a stronger relationship between the thickness of BNC samples and their ultimate load in vancomycin (FIG. 2).

Moreover, a stronger relationship between the thickness of the samples and their ultimate load was shown: R2=0.236 for BNC+Novochizol™+vancomycin, compared to R2=0.0405 for native BNC. Using factor analysis, it was possible to show a significant effect of cross-linked chitosan on the ultimate stress (p-value=0.005).

Further, the usefulness of impregnated bacterial cellulose was used in experimental animals (rats) which underwent cranial surgery with removal of a small section of dura matter, followed by duraplasty using ETHISORB™ Dura Patch dural substitute (A) and bacterial cellulose impregnated with cross-linked chitosan and vancomycin (B). (FIG. 2)

The bacterial cellulose impregnated with the cross-linked chitosan presents the following advantages over all other existing dural substitutes:

Chitosan-specific anti-inflammatory properties

The capacity to encapsulate, retain and sustainably release active ingredients (such as vancomycin)

Higher tensile strength

Higher flexibility

Transparency: this unique feature allows to visually inspect underlying tissue for any surgery-related injuries or abnormalities (FIG. 2).

One can strikingly observe the absence of brain tissue adherence formation after using the obtained impregnated bacterial cellulose (BNC), such adherences being a known complication after standard duraplasty.

Example 5: Cross-Linked Chitosan Coating of Magnetic Beads for Capture and Isolation of Nucleic Acids Pure or silica-coated magnetic beads are used for nucleic acid isolation in PCR diagnostics. The ability of cross-linked chitosan-coated magnetic beads to capture and release nucleic acid was confirmed in a series of PCR experiments aimed at amplifying DNA or RNA of viral pathogens at poultry farms with confirmed viral outbreaks as follows.

Three such outbreaks were chosen: (1) avian influenza A RNA virus, (2) chicken anemia DNA virus and (3) infectious bronchitis RNA virus. In each case, tested samples consisted of tissue homogenates (trachea, lungs, liver, kidney) pooled from 20 chicken from the affected poultry farms.

The performance of coating magnetic beads was compared to uncoated beads supplied in a commercial PCR diagnostic kit (RealBest™ vector-best.ru/en/) using the protocol recommended by the manufacturer.

Figure 3:
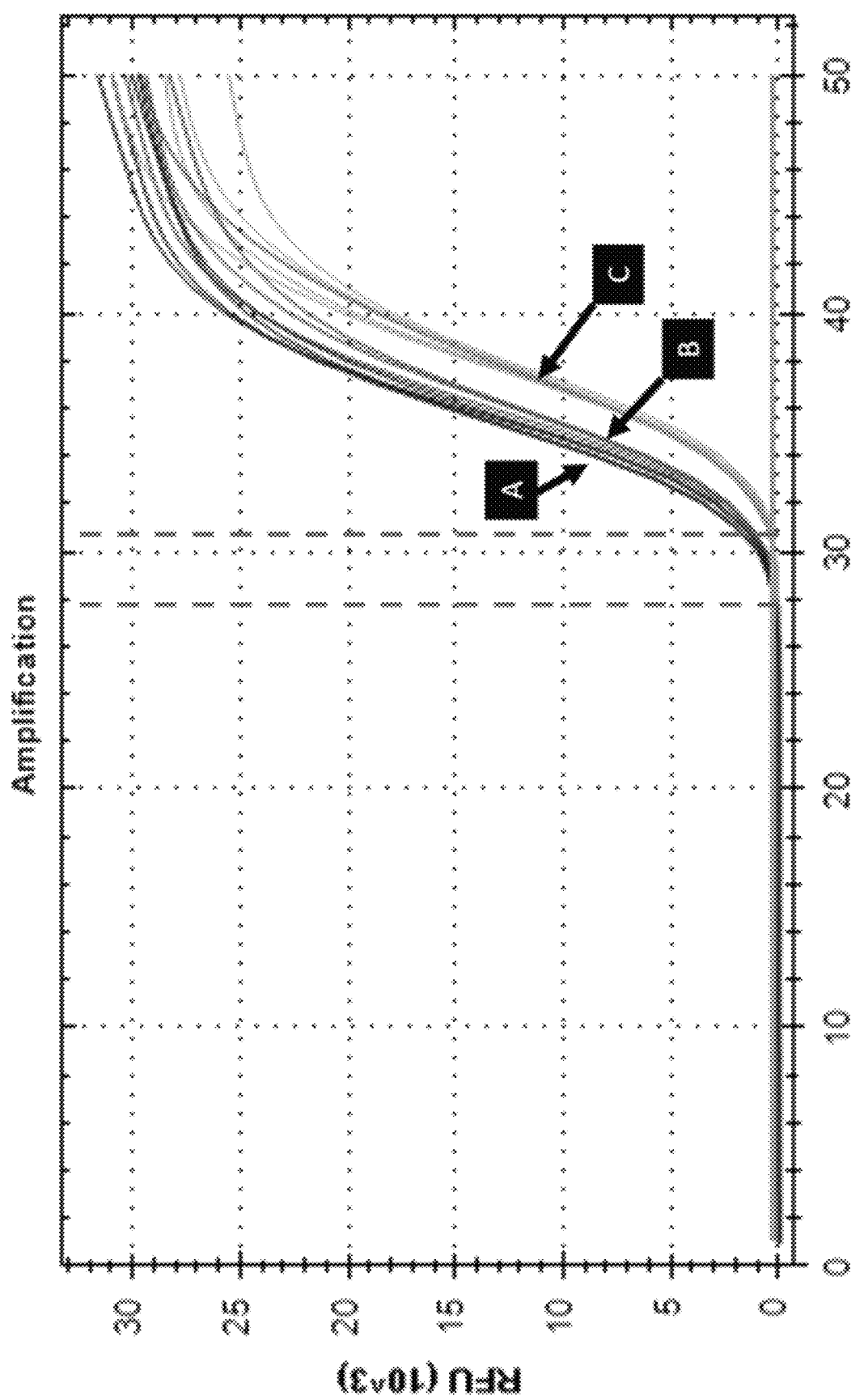
FIG. 3 shows the results of real time RT-PCR assays of Infectious Bronchitis Virus (IBV) (RNA marker) in tissue homogenates (trachea, lungs, liver, kidney) pooled from 20 chicken from a poultry farm with confirmed viral outbreak. Nucleic acid isolation and PCR were carried out using RealBest kits (vector-best.ru/en/) with either the supplied magnetic beads without any modification (C) or coated with cross-linked chitosan (A and B) as described in Example 6.

For RT-PCR Assay of Infectious Bronchitis Virus) cross-linked chitosan-coated beads allowed a 2 to 3 cycle gain in RT-PCR (FIG. 3). In another instance, variants of cross-linked chitosan containing additional cross-linkers were shown to irreversibly capture all nucleic acids present in different samples (DNA and RNA).

Those data support that both plain and silica-coated magnetic beads may be easily coated with a cross-linked chitosan for more sensitive and more specific regular and real-time PCR assays, in particular from sources that contain PCR inhibitor, such as:

1. Animal samples rich in iron (Hemoglobin in blood, myoglobin in muscles; lactoferrin in milk and other inhibitors).
2. Plant tissues (triterpenoids and other inhibitors).

Example 6: A Method of Preparation of Highly Biocompatible and Long-Lasting Suture Threads A 300 µm thick bacterial cellulose filament is immersed in a solution containing 10% wt. Polyvinyl alcohol, 2% of soluble cross-linked chitosan (Novochizol™), 1% Vancomycin and incubated for 30 minutes at room temperature.

The filament is then extruded through a 400 µm diameter nozzle heated to +80° C. at a speed of 50-100 cm per minute and immediately wound in a single layer on a 200 mm diameter stainless steel reel, cooled to −20° C. During winding, tension is applied to ensure that the thread does not sag and that it is pulled through the nozzle to avoid deformation of the thread when it contacts the spool. During the winding process, the thread is thus "frozen in place".

Then spool is sealed to avoid any desiccation and kept at −20° C. for 10-12 hours.

Then spool is then warmed; first to −5° C., without controlling the warming rate, and then to +2° C., at a rate of 0.01-0.03° C.° C. per minute.

Complete thawing of the frozen filament, is assessed visually by an increase in transparency of the thread.

The filament is wound on a plastic spool with a diameter of 50 mm, packed in a sealed bag, and sterilized in an electron beam.

The invention claimed is:

1. An aqueous gelling solution comprising a gel-forming polymer from about 0.3% to about 25% (w/w), a biocompatible acid and a soluble cross-linked chitosan at 0.001% and 20% (w/w),
   wherein said soluble cross-linked chitosan is fully soluble at pH <5.5 in aqueous solution at room temperature and said cross-linked chitosan having been formed by reacting chitosan with an acrylic compound of Formula (I) to form an acylation product and reacting the acylation product in the presence of a base:

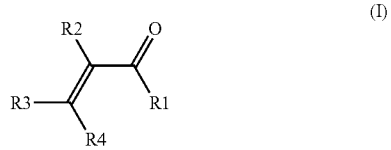

(I)

wherein $R_1$ is a halogen or any other leaving group that upon removal, ensures acylation of an amino group, anhydride, mixed anhydrides, N-hydroxysuccinimide, pentachlorophenol, 2-nitro-4-sulfophenol esters and other similar leaving groups; $R_2$, $R_3$ and $R_4$ are independently selected from H; optionally substituted alkyl, optionally substituted alkenyl, optionally substituted alkynyl, optionally substituted cycloalkyl, optionally substituted cycloalkenyl, optionally substituted cycloalkynyl, optionally substituted heterocycloalkyl; optionally substituted aryl, optionally substituted heteroaryl and optionally substituted aryl $C_1$-$C_6$ alkyl; wherein the term "substituted" refers to groups substituted with from 1 to 5 substituents selected from the group consisting of halogen, —COOR', —NR'R", —O, —OR', —COR', —CONR'R", —SR', —SO$_3$R', —SO$_2$NR'R", —SOR', —SO$_2$R', —NO$_2$, or —CN; or $R_1$ and $R_2$ or $R_1$ and $R_3$, or $R_1$ and $R_4$ together form an optionally substituted 4-24 membered aryl, heteroaryl, cycloalkyl or heterocycloalkyl, wherein said biocompatible acid is selected from acetic acid, citric acid, propionic acid, caproic acid, aminocaproic acid, succinic acid, glutaric acid, lactic acid, malic acid, tartaric acids, cinnamic acid and benzoic acid, sorbic acid, oxalic acid, salicylic acid, acetylsalicylic and cinnamon acid and wherein said soluble cross-linked chitosan is characterized by the presence of a hydrolysis product of Formulae IIIa or IIIb

(IIIa)

(IIIb)

when said cross-linked chitosan is subjected to an acidic hydrolysis and $R_2$, $R_2'$, $R_3$, $R_3'$, $R_4$ and $R_4'$ are independently selected from H; optionally substituted alkyl, optionally substituted alkenyl, optionally substituted alkynyl, optionally substituted cycloalkyl, optionally substituted cycloalkenyl, optionally substituted cycloalkynyl, optionally substituted heterocycloalkyl; optionally substituted aryl, optionally substituted heteroaryl and optionally substituted aryl $C_1$-$C_6$ alkyl; wherein the term "substituted" refers to groups substituted with from 1 to 5 substituents selected from the group consisting of halogen, —COOR', —NR'R", =O, —OR', —COR', —CONR'R", —SR', —SO$_3$R', —SO$_2$NR'R", —SOR', —SO$_2$R', —NO$_2$, or —CN; or $R_1$ and $R_2$ or $R_1$ and $R_3$, or $R_1$ and $R_4$ together form an optionally substituted 4-24 membered aryl, heteroaryl, cycloalkyl or heterocycloalkyl.

2. The aqueous gelling solution according to claim 1, wherein the gel-forming polymer is a polymer or a mixture of polymers selected from a polyethylene, a polyacrylamide, a polystyrene, an agarose polymer, an alginate polymer, a DNA polymer, a cellulose-based polymer, a hyaluronic acid hydrogel and a polyethylene glycol hydrogel.

3. A method for the preparation of a polymeric composite material in the form of a cryogel said method comprising:
   providing gelling solution according to claim 1, at a temperature higher than 0° C. but below the boiling temperature;
   subjecting the said gelling solution to a gelling-thawing step, wherein the said gelling solution is first frozen (gelling step) and then warmed until thawing at warming rate not higher than about 1° C. per minute when the temperature reaches −6° C. and above; and isolating the obtained macroporous cryogel.

4. A method for the preparation of a polymeric composite material in the form of a gel said method comprising:

providing gelling solution according to claim 1, at a temperature higher than 0° C. but below the boiling temperature;

subjecting the said gelling solution to a gelation step other than cryo-gelation; and isolating the obtained gel.

5. A method of cell printing comprising:

providing a first volume of a gelling solution according to claim 1, wherein said first volume of gelling solution is free of cells (cell-free solution) and printing it on solid surface made of a thermo-conductive material which is cooled to a temperature between −10° C. and −20° C.;

providing a second volume of said gelling solution, wherein said second volume of a gelling solution further contains a cryoprotectant and cells (cell containing solution) and printing the mixture on top of the printed layer of already printed gelling solution;

repeating sequentially the steps above until the desired number of cell layers have been printed in order to form a multi-layered 3D construct; and subjecting the multi-layered 3D constructs to a gelling-thawing step.

6. A surgical material comprising cellulose, impregnated with a soluble cross-linked chitosan or a gelling solution according to claim 1, wherein said material is impregnated with at least 0.001% w/w soluble cross-linked chitosan.

7. The surgical material according to claim 6, wherein said material is selected from suture threads or a dural substitute.

8. A plain or silica-coated magnetic bead coated with a soluble cross-linked chitosan or a gelling solution according to claim 1, wherein said beads are coated with at least 0.001% w/w soluble cross-linked chitosan.

9. The aqueous gelling solution according to claim 1, wherein the soluble cross-linked chitosan is obtained by a method comprising the following steps:

a) providing a chitosan and leaving the said chitosan to swell in a solvent;

b) acylating the amino groups of said chitosan with an acrylic compound of Formula (I):

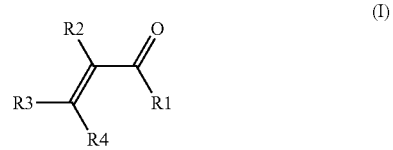

wherein $R_1$ is an a halogen or any other leaving group that upon removal, ensures acylation of an amino group, anhydride, mixed anhydrides, N-hydroxysuccinimide, pentachlorophenol, 2-nitro-4-sulfophenol esters and other similar leaving groups; $R_2$, $R_3$ and $R_4$ are independently selected from H; optionally substituted alkyl, optionally substituted alkenyl, optionally substituted alkynyl, optionally substituted cycloalkyl, optionally substituted cycloalkenyl, optionally substituted cycloalkynyl, optionally substituted heterocycloalkyl; optionally substituted aryl, optionally substituted heteroaryl and optionally substituted aryl $C_1$-$C_6$ alkyl; wherein the term "substituted" refers to groups substituted with from 1 to 5 substituents selected from the group consisting of halogen, —COOR', —NR'R", =O, —OR', —COR', —CONR'R", —SR', —SO$_3$R', —SO$_2$NR'R", —SOR', —SO$_2$R', —NO$_2$, or —CN; or $R_1$ and $R_2$ or $R_1$ and $R_3$, or $R_1$ and $R_4$ together form an optionally substituted 4-24 membered aryl, heteroaryl, cycloalkyl or heterocycloalkyl;

c) reacting the acylation product of step b) in the presence of a base (Aza-Michael reaction);

d) purifying the cross-linked chitosan obtained from step c).

* * * * *